US008268577B2

(12) United States Patent
Rishpon et al.

(10) Patent No.: US 8,268,577 B2
(45) Date of Patent: Sep. 18, 2012

(54) ELECTROCHEMICAL METHODS OF DETECTING COLON CANCER CELLS AND USE OF SAME FOR DIAGNOSING AND MONITORING TREATMENT OF THE DISEASE

(75) Inventors: Judith Rishpon, Rechovot (IL); Rachela Popovtzer, Givat Shmuel (IL); Yosi Shacham-Diamand, Zikhron-Yaakov (IL); Tova Neufeld, Ariel (IL); Sefi Vernick, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 526 days.

(21) Appl. No.: 12/379,974

(22) Filed: Mar. 5, 2009

(65) Prior Publication Data
US 2009/0232740 A1 Sep. 17, 2009

Related U.S. Application Data

(63) Continuation-in-part of application No. PCT/IL2008/000457, filed on Apr. 2, 2008.

(60) Provisional application No. 60/907,441, filed on Apr. 2, 2007.

(51) Int. Cl.
*C12Q 1/42* (2006.01)
(52) U.S. Cl. ............................................................ 435/21
(58) Field of Classification Search .................... 435/21
See application file for complete search history.

(56) References Cited

U.S. PATENT DOCUMENTS

| 6,682,648 | B1 * | 1/2004 | MacPhee et al. | 205/777.5 |
| 2006/0216704 | A1 * | 9/2006 | Newton et al. | 435/5 |
| 2010/0243479 | A1 * | 9/2010 | Choi et al. | 205/777.5 |

FOREIGN PATENT DOCUMENTS

| CN | 1588078 | 3/2005 |
| WO | WO 91/15595 | 10/1991 |
| WO | WO 2008/120216 | 10/2008 |

OTHER PUBLICATIONS

Popovtzer R. et al. Electrochemical Detection of Biological Reactions Using a Novel Nano Biochip Array. Sensors and Actuators B 119:664-672, 2006.*
Wei J. et al. High Molecular Mass Alkaline Phosphatase as a Tumor Marker for Colorectal Cancer. Clinical Chemistry 39(3)540-543, Mar. 1993.*
International Preliminary Report on Patentability Dated Oct. 15, 2009 From the International Bureau of WIPO Re.: Application No. PCT/IL2008/000457.
International Search Report and the Written Opinion Dated Jul. 10, 2008 From the International Searching Authority Re.: Application No. PCT/IL2008/000457.
Du et al. "Immunological Assay for Carbohydrate Antigen 19-9 Using an Electrochemical Immunosensor and Antigen Immobilization in Titania Sol-Gel Matrix", Journal of Immunological Methods, XP004476979, 283(1-2): 67-75, Dec. 1, 2003.
Kokado et al. "New Electrochemical Assay of Alkaline Phosphatase Using Ascorbic Acid 2-Phosphatase and Its Application to Enzyme Immunoassay", Analytica Chimica Acta, XP002486110, 407(1-2): 119-125, Feb. 29, 2000.
Lin et al. "Electrochemical and Chemiluminescent Immunosensors for Tumor Markers", Biosensors & Bioelectronics, XP004697364, 20(8): 1461-1470, Feb. 15, 2005.
Popvtzer et al. "Electrochemical Detection of Biological Reactions Using a Novel Nano-Bio-Chip Array", Sensors and Actuators B, XP005661830, 119(2):664-672, Dec. 7, 2006. Abstract, p. 665-670, § 2.1, 2.2.2-2.2.4, 3.1.2, 4.
Communication Pursuant to Article 94(3) EPC Dated Feb. 19, 2010 From the European Patent Office Re.: Application No. 08720067.1.
Response Dated Jun. 10, 2010 to Communication Pursuant to Article 94(3) EPC of Feb. 19, 2010 From the European Patent Office Re.: Application No. 08720067.1.
Communication Pursuant to Article 94(3) EPC Dated Sep. 28, 2010 From the European Patent Office Re. Application No. 08720067.1.
Response Dated Dec. 22, 2010 to Communication Pursuant to Article 94(3) EPC of Sep. 28, 2010 From the European Patent Office Re. Application No. 08720067.1.
Walach et al. "Leukocyte Alkaline Phosphatase as a Probable Predictor of the Metastatic State in Breast ans Colon Cancer Patients", Oncology, XP008127126, 52(1): 12-18, 1995.
Result of Consultation Dated Feb. 8, 2011 From the European Patent Office Re.: Application No. 08720067.1.
Summons to Attend Oral Proceedings Pursuant to Rule 115(1) EPC Dated Feb. 9, 2011 From the European Patent Office Re. Application No. 08720067.1.
Office Action Dated Oct. 11, 2011 From the Israel Patent Office Re. Application No. 201258 and Its Translation Into English.
Astier et al. "The Measurement of Alkaline Phosphatase at Nanomolar Concentration Within 70 S Using a Disposable Microelectrochemical Transistor", Bioelectrochemistry, 64(1): 53-59, Aug. 2004. Abstract.
Basson et al. "Differential Modulation of Human (Caco-2) Colon Cancer Cell Line Phenotype by Short Chain Fatty Acids", Proceedings of the Society of Experimental Biology and Medicine, 217(4): 476-483, Apr. 1998. Abstract.
Palmer et al. "Flow Injection Electrochemical Enzyme Immunoassay for Theophylline Using a Protein a Immunoreactor and P-Aminophenyl Phosphate-P-Aminophenol as the Detection System", The Analyst, 117(11): 1679-1682, Nov. 1992. Abstract.
Translation of Office Action dated Mar. 21, 2012 From the State Intellectual Property Office of the People's Republic of China Re. Application No. 200880018299.6.
Chen et al. "The Effect of Butyrate on the Proliferation and Differentiation of Human Colon Cancer Cell Line SW1116", Journal of Surgery Concepts and Practice, 8(3): 199-203, Aug. 3, 2003. English Abstract.

* cited by examiner

*Primary Examiner* — Ralph Gitomer

(57) ABSTRACT

A method of detecting cancer cells is disclosed. The method comprises (a) contacting the cell with a substrate for an enzyme under conditions wherein the enzyme catalyzes a reaction of the cell with the substrate, so as to generate a product capable of producing an electrical signal; and (b) measuring a level of the electrical signal, wherein a difference in a level of the electrical signal compared to a predetermined threshold is indicative of a cancer cell. The method may be adapted for diagnosis, monitoring a cancer therapy, identifying agents capable of treating cancer and individually optimizing a cancer therapy.

27 Claims, 14 Drawing Sheets
(12 of 14 Drawing Sheet(s) Filed in Color)

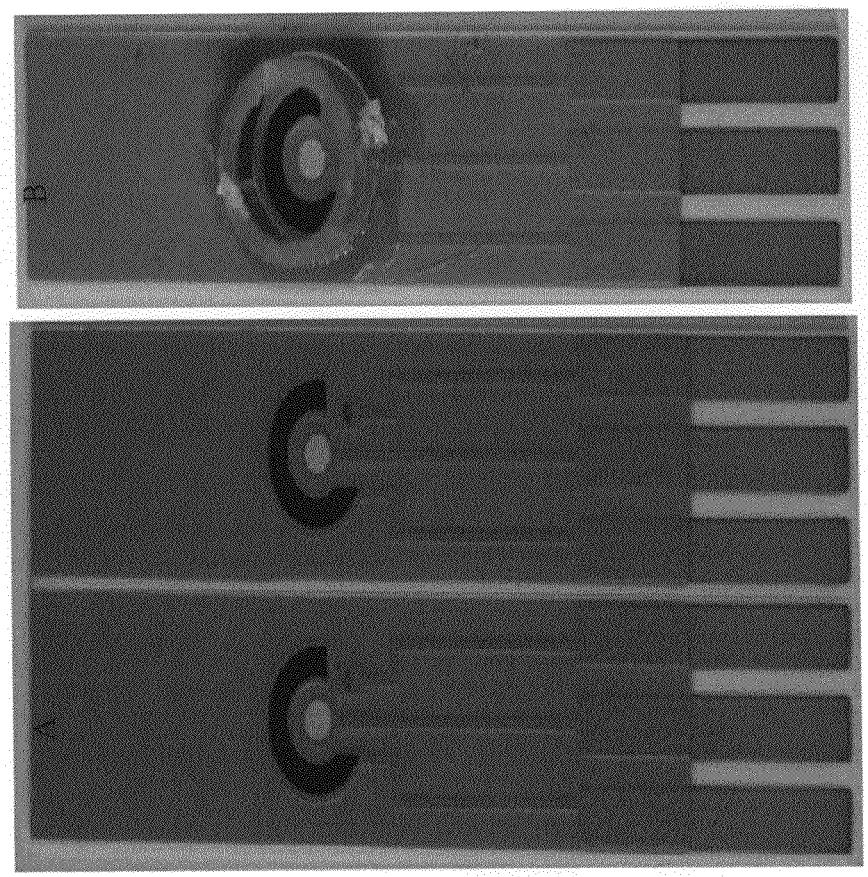
FIGs. 7A-B

ELECTROCHEMICAL METHODS OF DETECTING COLON CANCER CELLS AND USE OF SAME FOR DIAGNOSING AND MONITORING TREATMENT OF THE DISEASE

RELATED APPLICATIONS

This application is a Continuation-In-Part of PCT Patent Application No. PCT/IL2008/000457, filed on Apr. 2, 2008, which claims the benefit of U.S. Provisional Patent Application No. 60/907,441, filed on Apr. 2, 2007. The contents of the above Applications are all incorporated herein by reference.

FIELD AND BACKGROUND OF THE INVENTION

The present invention relates to a method of detecting cancer and, more particularly, to methods of optimizing drug treatment for cancer.

Cancer is responsible for the majority of morbidity and mortality worldwide, despite recent advances in medical technology. Current therapeutic strategies focus predominantly on achieving the removal or death of cancer cells within the patient, through a diverse array of surgical and non-surgical techniques; the most widely used are chemotherapy and gamma irradiation. Those methods have a number of prominent disadvantages, in particular the culling of healthy cells/tissues within the patient, and the rather toxic side-effects of the current generation of chemotherapeutic drugs utilized in cancer treatment.

'Differentiation therapy' is an alternative approach which promotes reversion of phenotype from malignant to normal. Differentiation therapy is based on the concept that cancer cells are normal cells that have been arrested at an immature or less differentiated state, lack the ability to control their own growth, and thus multiply at an abnormally fast rate. Differentiation therapy aims to force the cancer cell to resume the process of maturation. Although differentiation therapy does not kill the cancer cells, it restrains their growth and allows the application of more conventional therapies (such as chemotherapy) to eradicate the remaining malignant cells.

Differentiation therapy has a number of advantages over conventional therapeutic strategies that target death of cancer/tumor cells. For a start, the culling of healthy cells/tissues within the patient with chemotherapeutic drugs or gamma irradiation would be eliminated, together with their associated adverse side-effects. In many cases, the killing of cancer cells through gamma irradiation or chemotherapeutic eliminates most, but not completely all cancer cells within the patient, thereby leading to remission of the disease. With differentiation therapy, it is speculated that by inducing some of the cancer cells into the pathway of terminal differentiation and eventual senescence, this would somehow signal other cancer cells to follow suit through a variety of mechanisms.

Various markers have been used as a means of monitoring patients undergoing differentiation therapy. One such marker is alkaline phosphatase, wherein expression of same was shown to correlate with the differentiation status of a cell [Patnaik A, et al., Clin. Can Research, 2002 July; 8(7):2142-8; Rephaeli A, Zhuk R, Nudelman A, 2000, Drug Develop. Res. Vol 50:379-391].

Rapid and easy detection of such markers with high sensitivity, selectivity and accuracy paves the way for tailoring therapeutic agent to specific patients—'personalized medicine'. This is of great importance in cancer therapy where it is now known that tumor treatment response cannot be predicted only from its type and anatomical location.

Until presently, there is no detection system for such markers which meets all these demands.

U.S. Pat. App. No. 20060100488 teaches detection of cancerous cells by directly monitoring the electrical response of the cells following application of an alternating current. WO 91/15595 teaches analysis of electrical conductivity of cancer cells for monitoring responsiveness to therapy and drug screening. Specifically, WO 91/15595 teaches monitoring the effectiveness of a particular agent to inhibit increases in the volume and number of cancer cells by analyzing electrical conductivity thereof. Accordingly, both these patent applications teach that the intrinsic electrical properties of a cancer cell may be used as markers for detection and monitoring of cancer cells.

U.S. Pat. Appl. No. 20040053425 teaches amperometric analysis of an analyte in a fluid, wherein the electrode comprises the current producing enzyme. U.S. Pat. Appl No. 20040053425 does not teach amperometric detection of intracellular markers.

U.S. Pat. No. 5,149,629, teaches amperometric analysis of markers, including cancer cell markers, wherein the electrode comprises antibodies capable of binding the markers thereto. The analysis is by substrate competition. U.S. Pat. No. 5,149,629 does not detect endogenous amperometric features of cancer cells.

Thus, amperometric detection of analytes has been shown to be an effective method for detection. However, until presently, amperometric detection has not been used for analyzing cellular enzymatic activities.

SUMMARY OF THE INVENTION

According to one aspect of the present invention there is provided a method of detecting a cancer cell comprising: (a) contacting the cell with a substrate for an enzyme under conditions wherein the enzyme catalyzes a reaction of the cell with the substrate, so as to generate a product capable of producing an electrical signal; and (b) measuring a level of the electrical signal, wherein a difference in a level of the electrical signal compared to a predetermined threshold is indicative of a cancer cell.

According to another aspect of the present invention there is provided a method of diagnosing a subject with cancer comprising: (a) contacting at least one cell in a sample of a subject with a substrate for an enzyme under conditions wherein the enzyme catalyzes a reaction of the cell with the substrate, so as to generate a product capable of producing an electrical signal; and (b) measuring a level of the electrical signal, wherein a difference in a level of the electrical signal compared to a predetermined threshold is indicative of cancer.

According to yet another aspect of the present invention there is provided a method of individually optimizing a treatment for cancer, the method comprising: (a) contacting at least one cancer cell in a sample of a subject with at least one anti cancer agent; (b) contacting the at least one cancer cell with a substrate for an enzyme, under conditions wherein the enzyme catalyzes a reaction of the cell with the substrate, so as to generate a product capable of producing an electrical signal; and (c) measuring a level of the electrical signal produced by the cell, wherein the level is indicative of an efficiency of the anti cancer agent to treat the cancer of the subject.

According to yet another aspect of the present invention there is provided a method of detecting a cancer tissue comprising (a) contacting a tissue with a substrate for an enzyme under conditions wherein the enzyme catalyzes a reaction of a cell of the tissue with the substrate, so as to generate a product capable of producing an electrical signal; and (b) measuring a level of the electrical signal, wherein a difference in a level of the electrical signal compared to a predetermined threshold is indicative of a cancer tissue.

According to still another aspect of the present invention there is provided a method of monitoring an anti cancer treatment in a subject, the method comprising: (a) administering at least one anti cancer agent to the subject; (b) detecting a presence or level of cancer cells in a sample of the subject following step (a) according to the method of the present invention, wherein the presence or level is indicative of a state of the cancer.

According to an additional aspect of the present invention there is provided a method of determining an anti-cancer treatment for a subject, the method comprising:
(a) analyzing a presence or level of cancer cells in a sample of the subject according to the method of the present invention;
(b) administering to the subject a therapeutic effective amount of an anti cancer agent according to the presence or level of cancer cells in the sample of the subject.

According to further features in preferred embodiments of the invention described below, the method further comprises repeating step (a) following step (b).

According to yet an additional aspect of the present invention there is provided a method of identifying an agent capable of reversing a malignant phenotype of a cell, the method comprising, (a) subjecting at least one cancer cell to an agent; (b) measuring a malignant phenotype of the cell following (a) and optionally prior to (a) according to the method of the present invention, wherein a reversion of phenotype is indicative of an agent capable of reversing a malignant phenotype of a cell.

According to yet an additional aspect of the present invention there is provided a kit comprising: (i) at least one component of an electrochemical cell, the electrochemical cell being adapted for holding at least one biological cell and for performing electrochemical measurement; and (ii) at least one anti-cancer agent.

According to still further features in the described preferred embodiments, the kit further comprises a substrate which is enzymatically reacted on by an enzyme of the biological cell to yield a reaction product giving rise to a redox reaction at an electrode of the electrochemical cell.

According to an additional aspect of the present invention there is provided a system configured for detecting a cancer cell according to the method of the present invention.

According to still further features in the described preferred embodiments, the at least one cell comprises a plurality of cells.

According to still further features in the described preferred embodiments, the sample comprises a tissue.

According to still further features in the described preferred embodiments, the measuring is performed using means for high output.

According to still further features in the described preferred embodiments, the means is selected from the group consisting of an automated sampling device, a liquid handling equipment, a dispenser, an electrode array, a robot, or any combination thereof.

According to still further features in the described preferred embodiments, the contacting is effected in vitro.

According to still further features in the described preferred embodiments, the contacting is effected ex vivo.

According to still further features in the described preferred embodiments, the sample comprises no more than 500 cells.

According to still further features in the described preferred embodiments, the biopsy sample comprises no less than 10 cells.

According to still further features in the described preferred embodiments, the enzyme is alkaline phosphatase.

According to still further features in the described preferred embodiments, the substrate is p-APP.

According to still further features in the described preferred embodiments, the cancer cells are colon cancer cells.

According to still further features in the described preferred embodiments, the measuring is effected using an electrochemical cell.

According to still further features in the described preferred embodiments, the measuring is effected in a multiwell array.

According to still further features in the described preferred embodiments, each well of the multiwell array comprises an electrochemical cell.

According to still further features in the described preferred embodiments, each well of the multiwell array is a nano-volume well.

According to still further features in the described preferred embodiments, the agent comprises a test composition.

According to still further features in the described preferred embodiments, the test composition is selected from the group consisting of a polynucleotide a polypeptide, a small molecule chemical, a carbohydrate, a lipid and a combination of same.

According to still further features in the described preferred embodiments, the agent comprises a test condition.

According to still further features in the described preferred embodiments, the test condition is a radiation condition.

According to still further features in the described preferred embodiments, the cell is intact.

According to still further features in the described preferred embodiments, the cancer cells are intact.

According to still further features in the described preferred embodiments, the cell is a mammalian cell.

According to still further features in the described preferred embodiments, the cancer cells are mammalian cells.

The present invention successfully addresses the shortcomings of the presently known configurations by providing a method of electrically detecting cancer cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
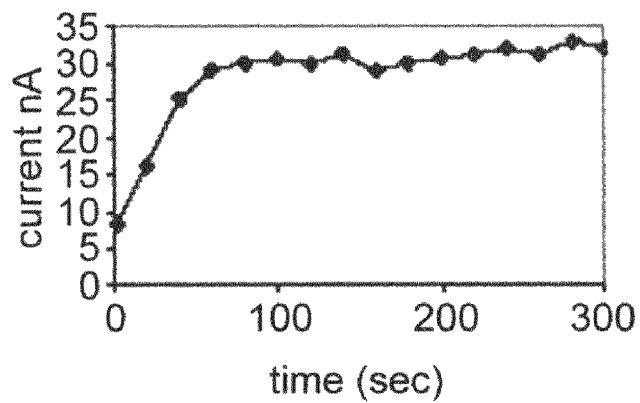
Figure 1B:
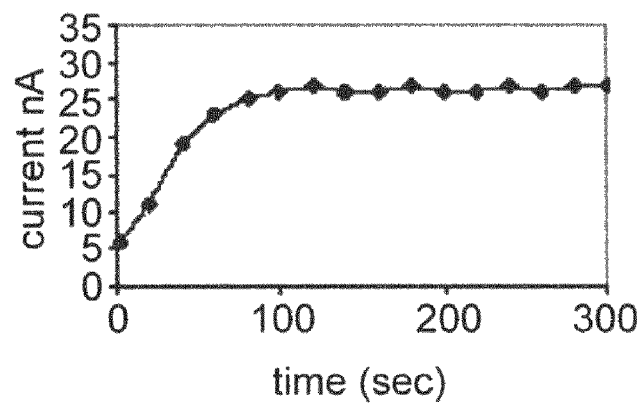
Figure 1C:
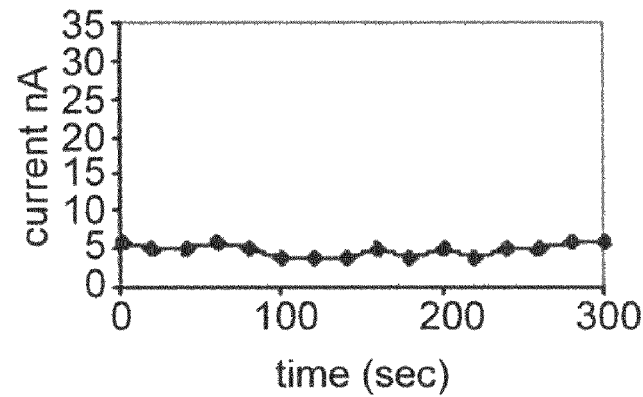

FIGS. 1A-C are graphs depicting the HT-29 colon cancer cell response to BA, butyroylmethyl-diethyl phosphate and pivaloyloxymethyl butyrate. Amperometric response curves for monitoring of alkaline phosphatase activity were generated using the electrochemical array chip. The HT-29 colon cancer cells were exposed to the following differentiation agents: Butyric acid (2.5 mM)—FIG. 1A, butyroylmethyl-diethyl phosphate and pivaloyloxymethyl butyrate (50 μM)—FIGS. 1B and 1C respectively. The HT-29 cells with the substrate PAPP were placed into the 100 nL volume electrochemical chambers on the chip. Current was measured using the amperometric technique at 220 mV. Error estimation (5 repeats) is 2 nA RMS.

Figure 2A:
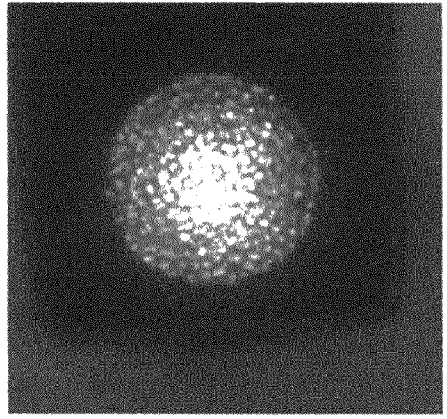
Figure 2D:
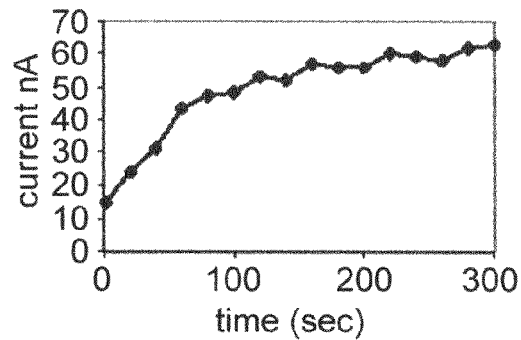
Figure 2B:
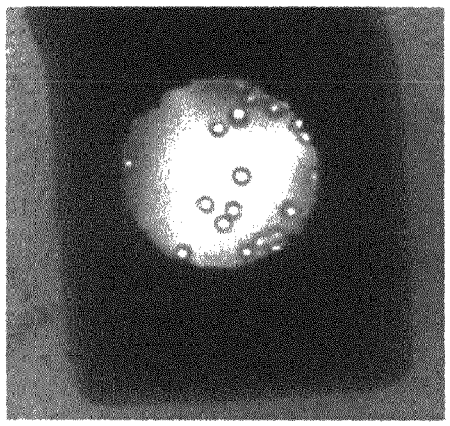
Figure 2E:
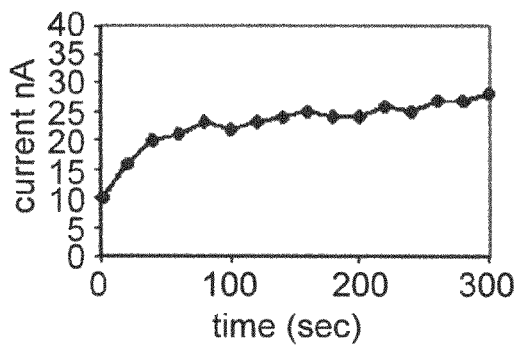
Figure 2C:
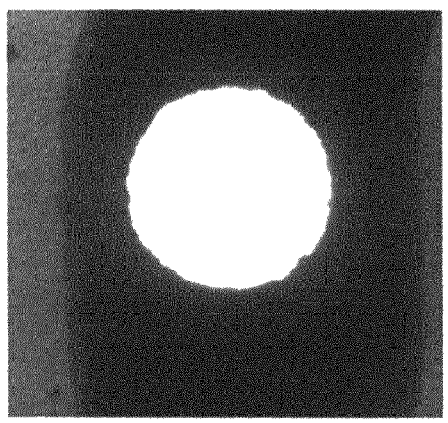

FIGS. 2A-C are photographs illustrating the number of cells per sample.

Figure 2F:
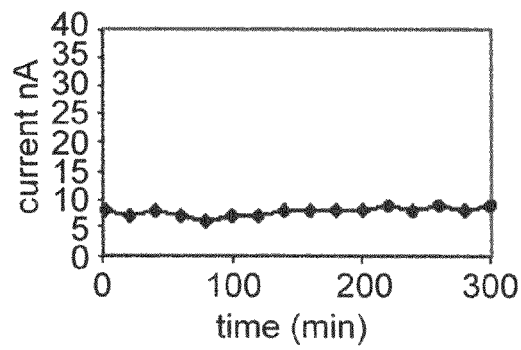

FIGS. 2D-F are graphs illustrating the enzymatic activities of the samples versus cell numbers. Error estimation (5 repeats) is 3 nA RMS.

Figure 3:
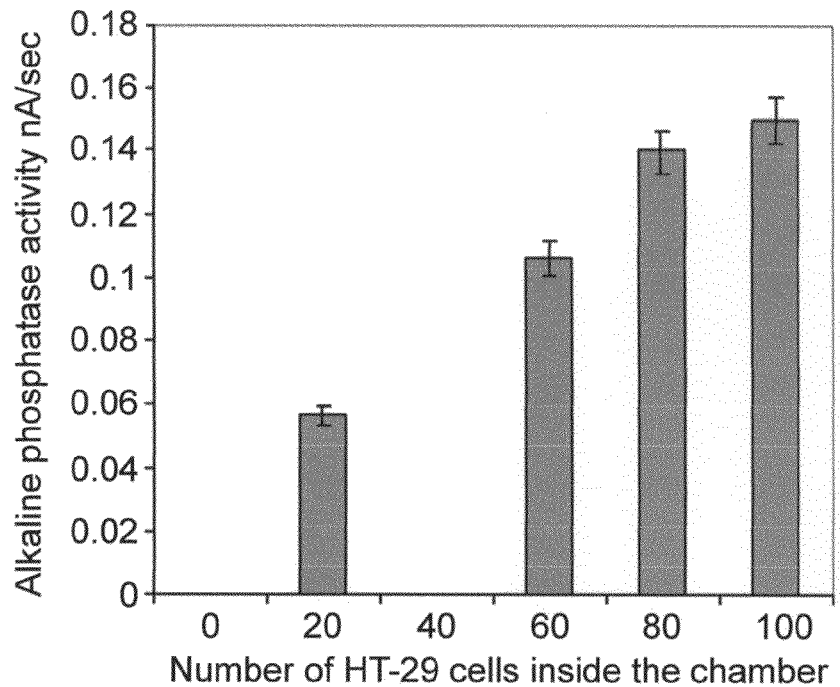

FIG. 3 is a bar graph depicting the correlation between HT-29 colon cancer cell number and the induced alkaline phosphatase enzymatic activity. Activity is presented by _current/_time. Each result represents the mean of three measurements. Current was measured using the amperometric technique at 220 mV.

Figure 4A:
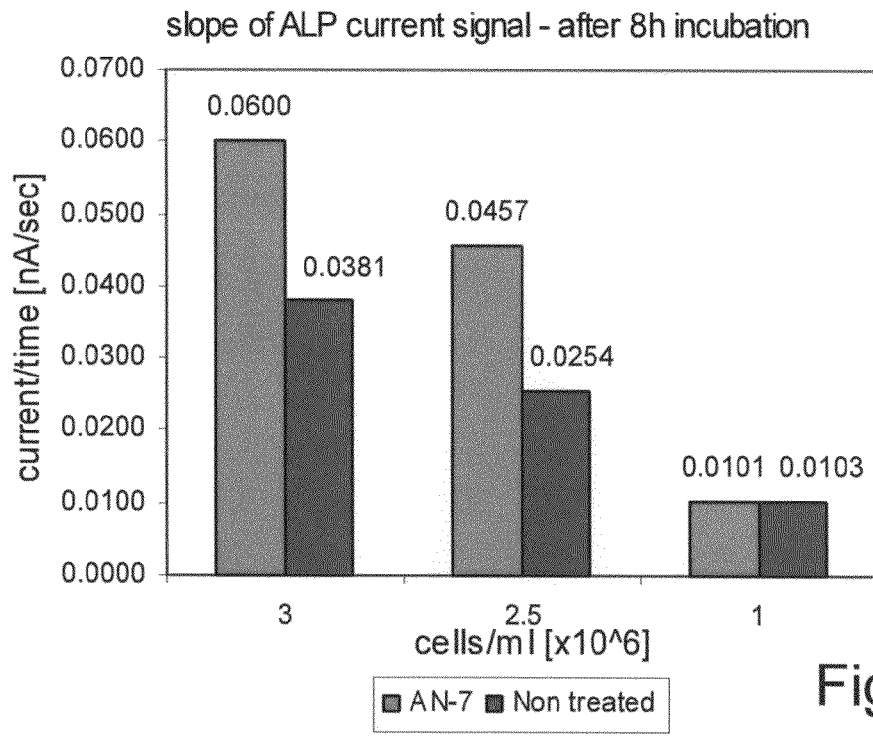
Figure 4B:
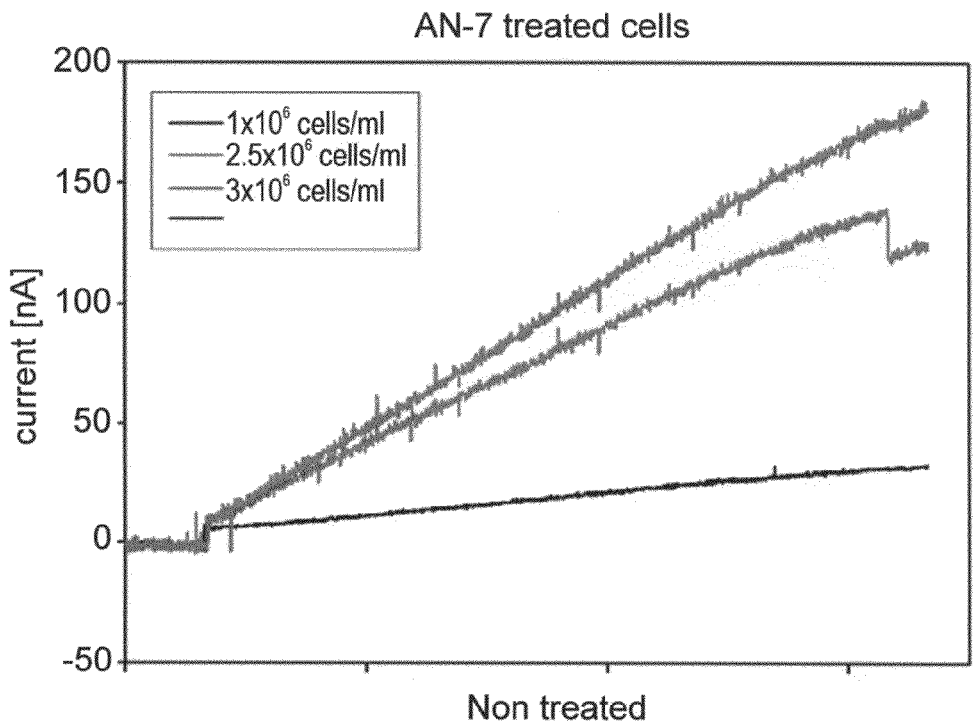
Figure 4C:
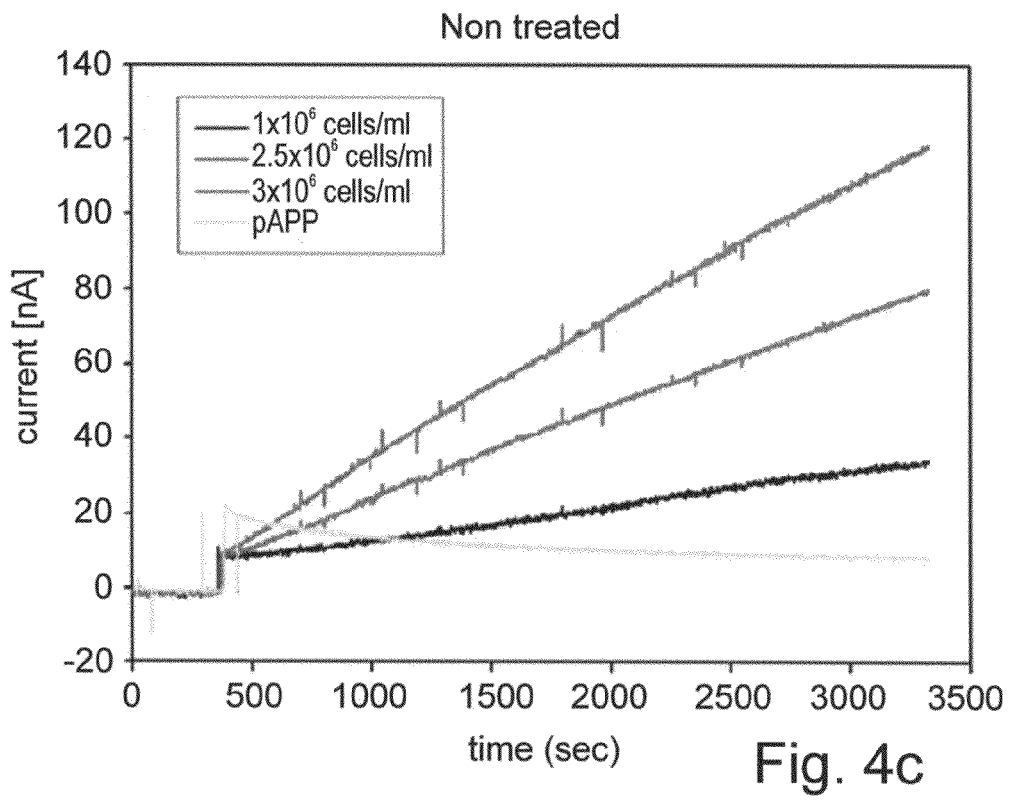

FIGS. 4A-C are graphs illustrating the effect of an eight hour treatment of butyroylmethyl-diethyl phosphate on HT-29 cells. FIG. 4A is a bar graph illustrating the slope of alkaline phosphatase current signal. FIGS. 4B-C are graphs illustrating the change in current over time, on different numbers of treated (FIG. 4B) and non-treated (FIG. 4C) cells.

Figure 5A:
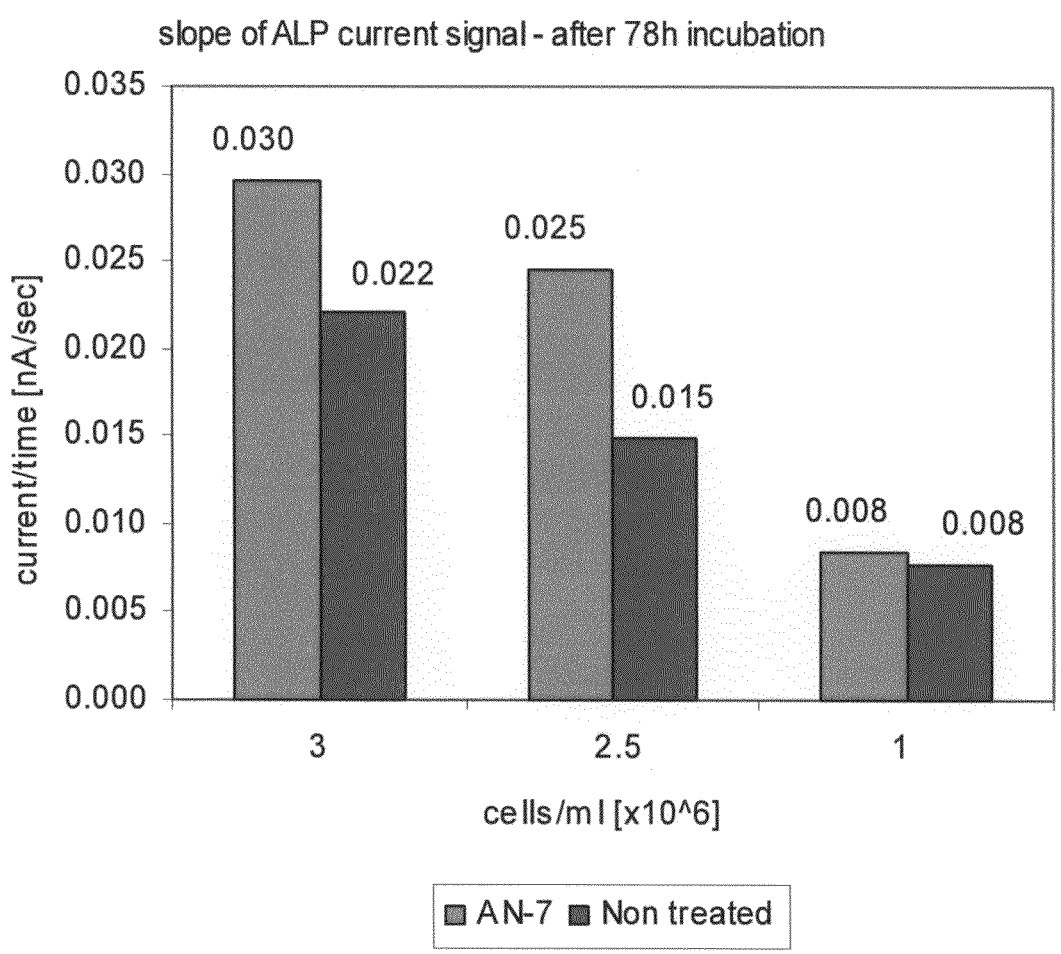
Figure 5B:
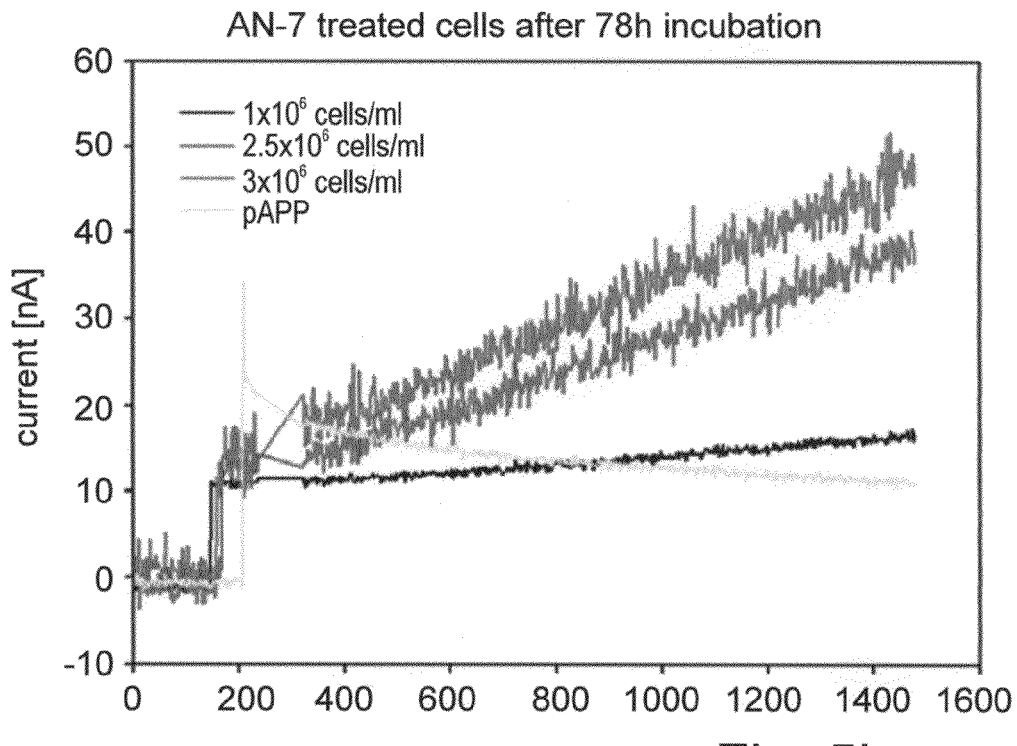
Figure 5C:
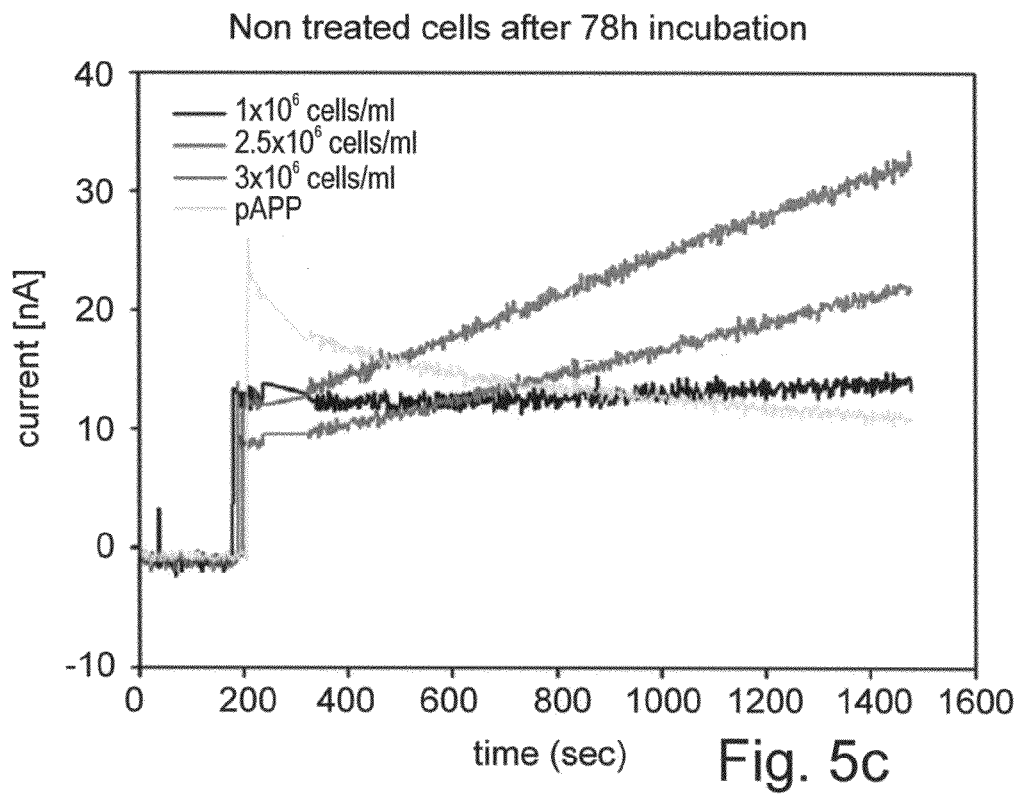

FIGS. 5A-C are graphs illustrating the effect of a seventy eight hour treatment of butyroylmethyl-diethyl phosphate on HT-29 cells. FIG. 5A is a bar graph illustrating the slope of alkaline phosphatase current signal. FIGS. 5B-C are graphs illustrating the change in current over time, on different numbers of treated (FIG. 5B) and non-treated (FIG. 5C) cells.

Figure 6A:
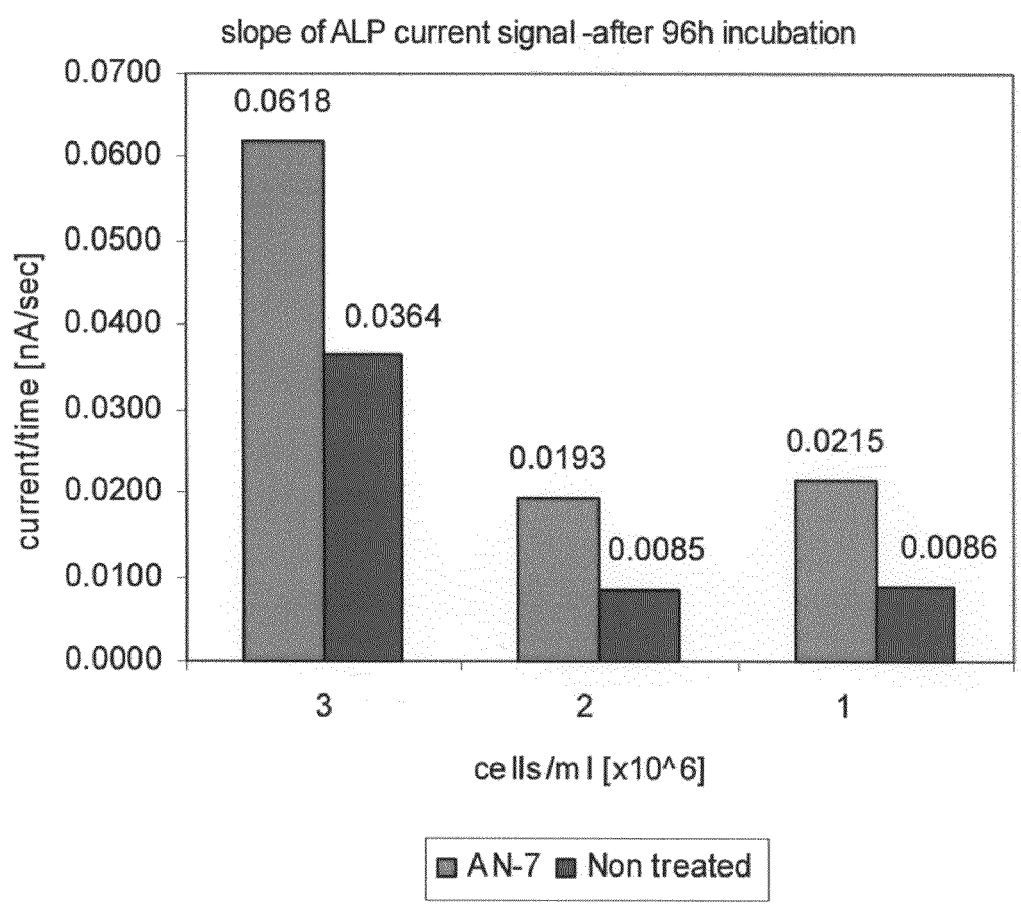
Figure 6B:
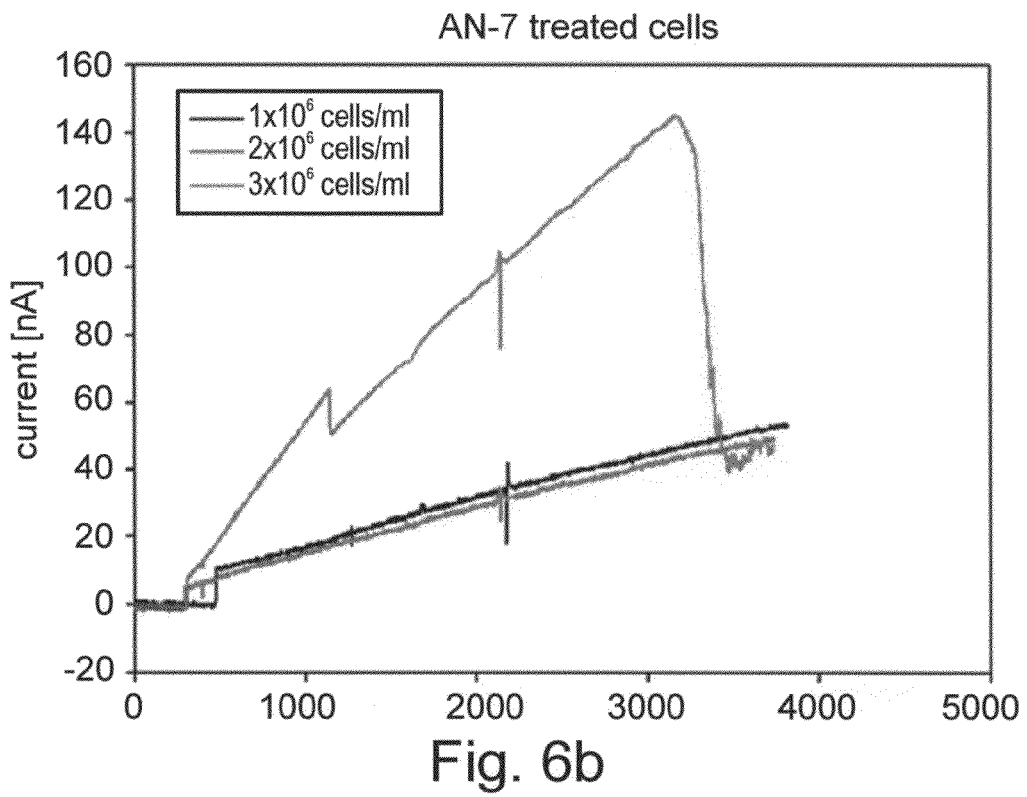
Figure 6C:
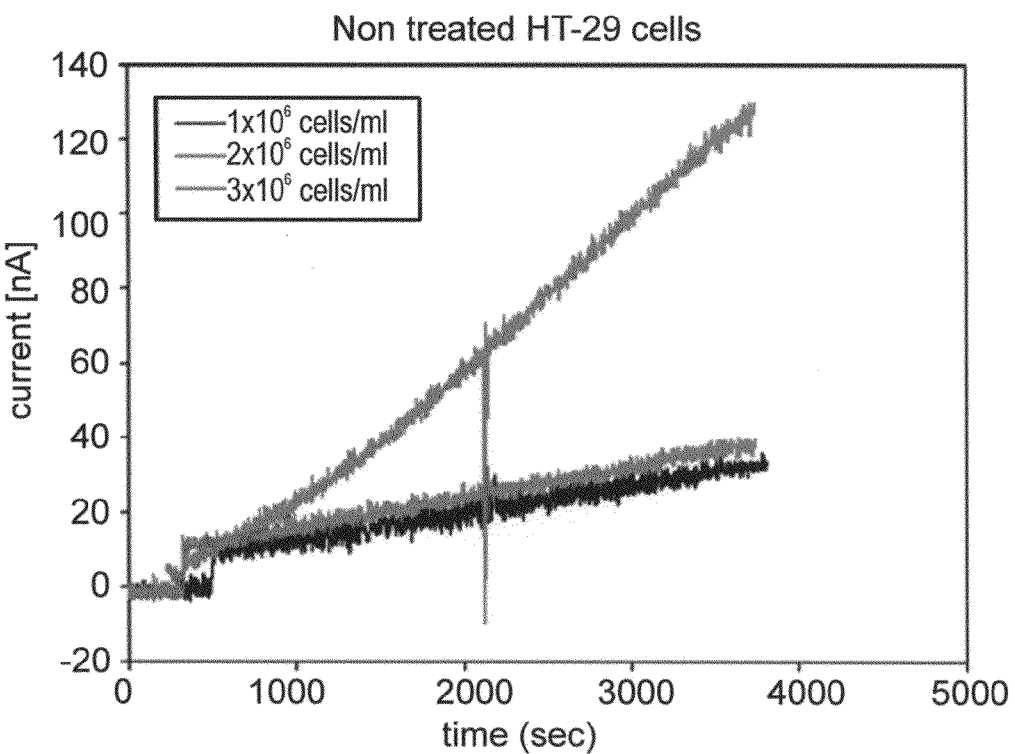

FIGS. 6A-C are graphs illustrating the effect of a ninety six hour treatment of butyroylmethyl-diethyl phosphate on HT-29 cells. FIG. 6A is a bar graph illustrating the slope of alkaline phosphatase current signal. FIGS. 6B-C are graphs illustrating the change in current over time, on different numbers of treated (FIG. 6B) and non-treated (FIG. 6C) cells.

FIGS. 7A-B are photographs of screen printed electrodes (FIG. 7A) and chambers (FIG. 7B) according to an embodiment of the present invention. The carbon (counter electrode), gold (working electrode) and Ag/AgCl (reference electrode) printed on ceramics (dimensions: 5 cm×1 cm) are shown in FIG. 7A. The electrochemical chamber was constructed as polystyrene tube glued to ceramics.

Figure 8:
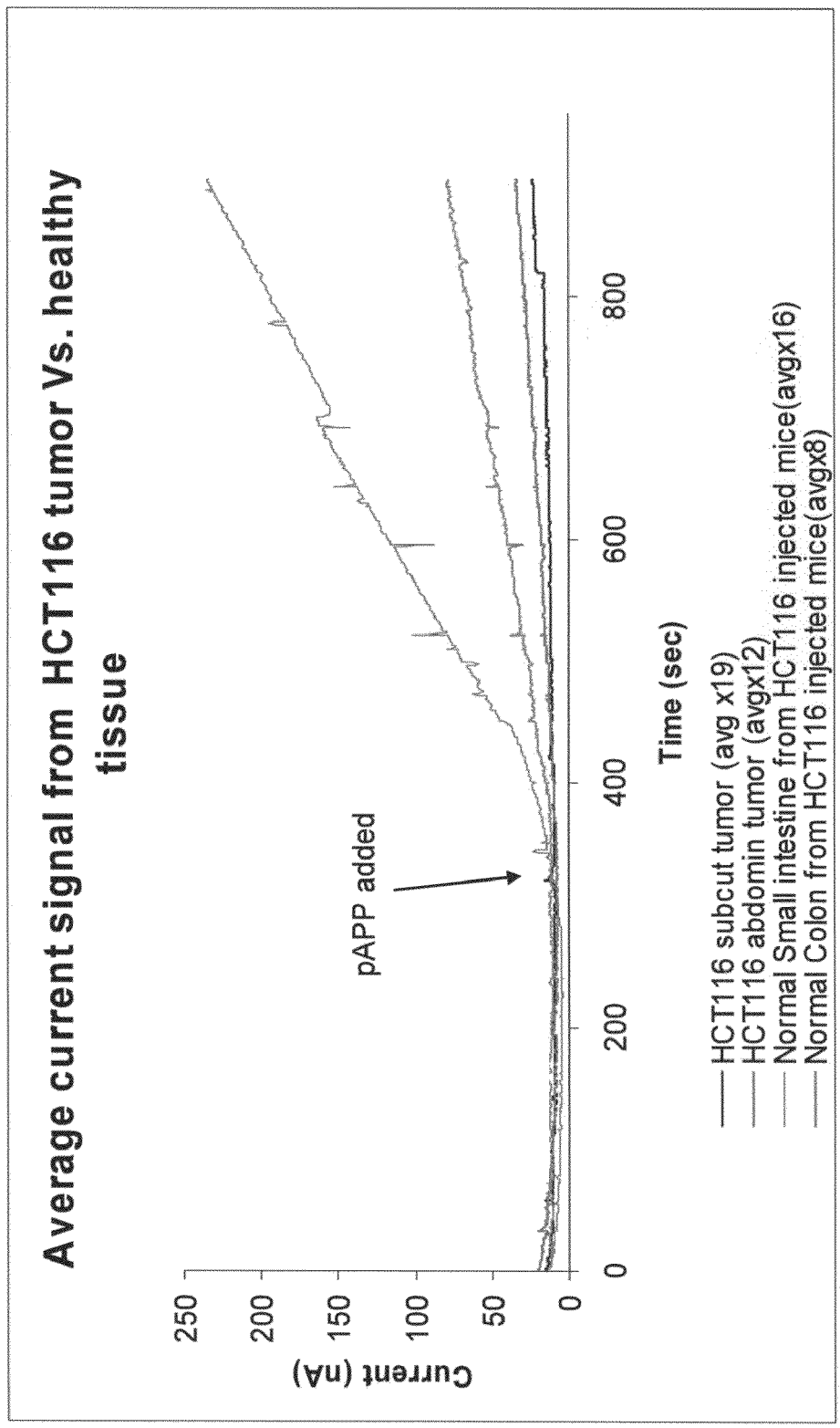

FIG. 8 is a graph illustrating the results of chronoamperometry analysis of HCT116 tumors and healthy tissues, indicating presence or absence of alkaline phosphates and hence cell differentiation state.

Figure 9:
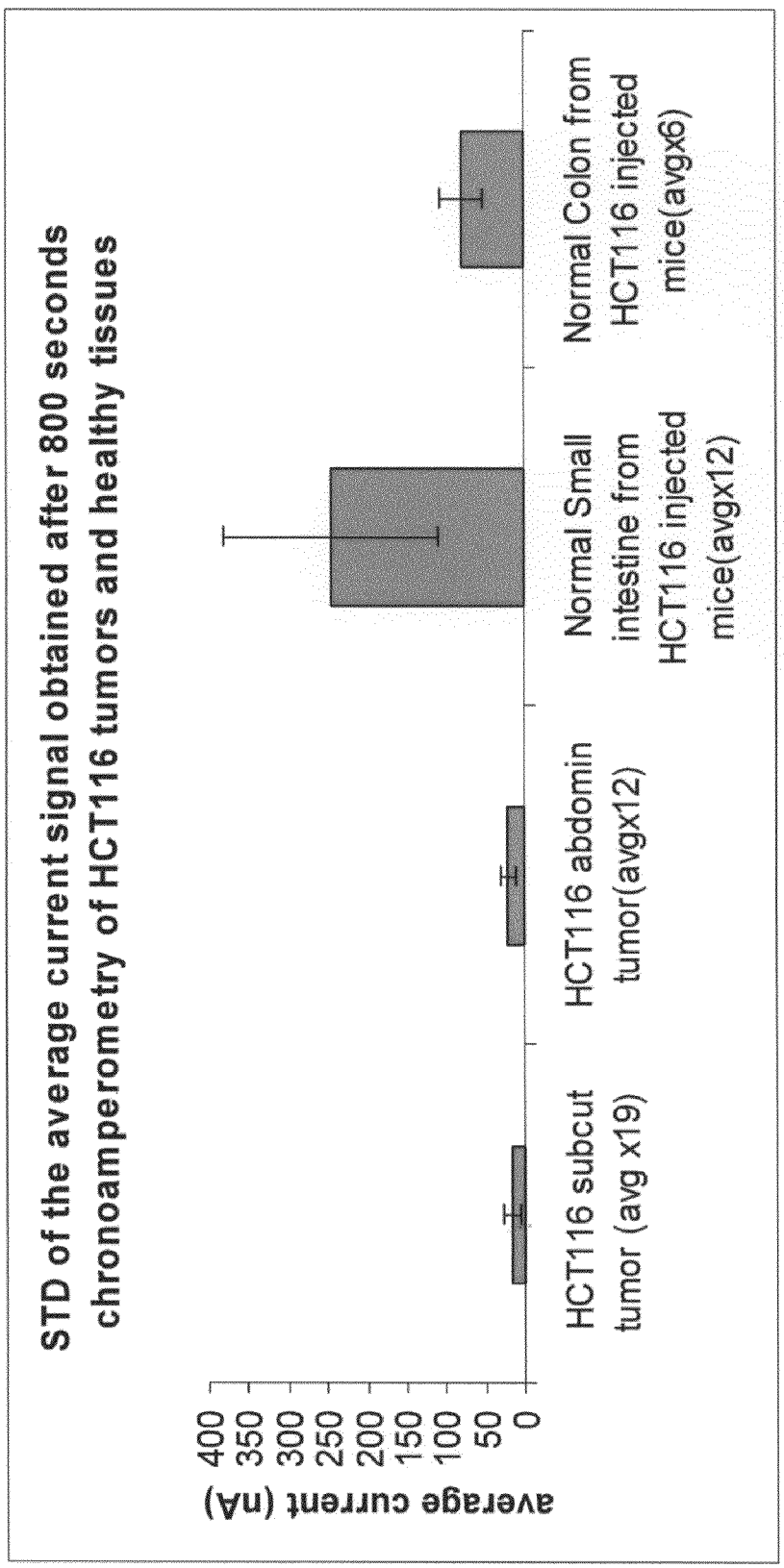

FIG. 9 is a graph illustrating the standard deviation from the average current signal obtained at 800 seconds (subcut=subcutaneous, abdomen=abdominal, avg=average) in HCT116 and healthy tumor slices.

Figure 10:
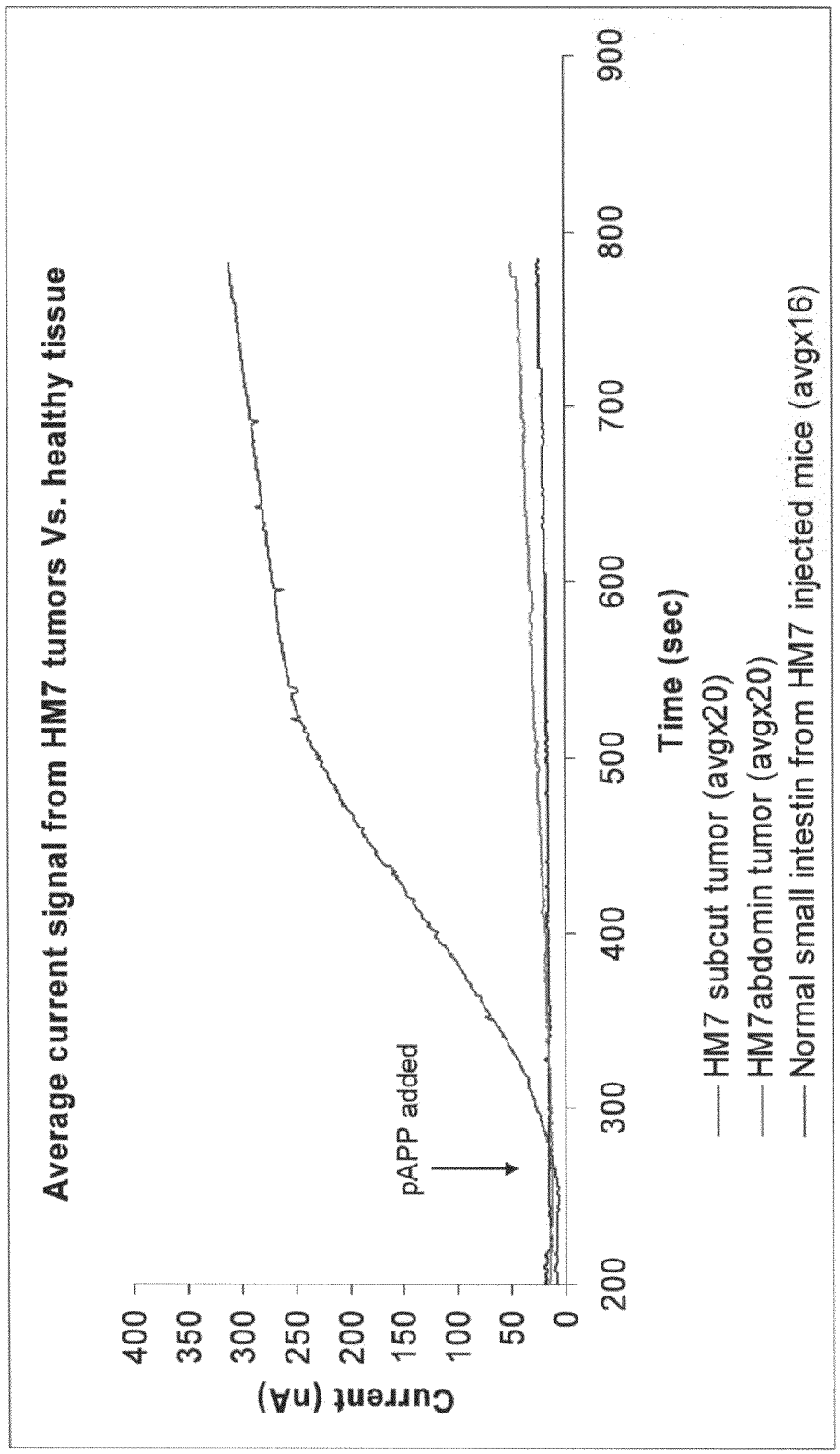

FIG. 10 is a graph illustrating the results of chronoamperometry analysis of HM7 tumors and healthy tissues, indicating presence or absence of alkaline phosphates and hence cell differentiation state.

Figure 11:
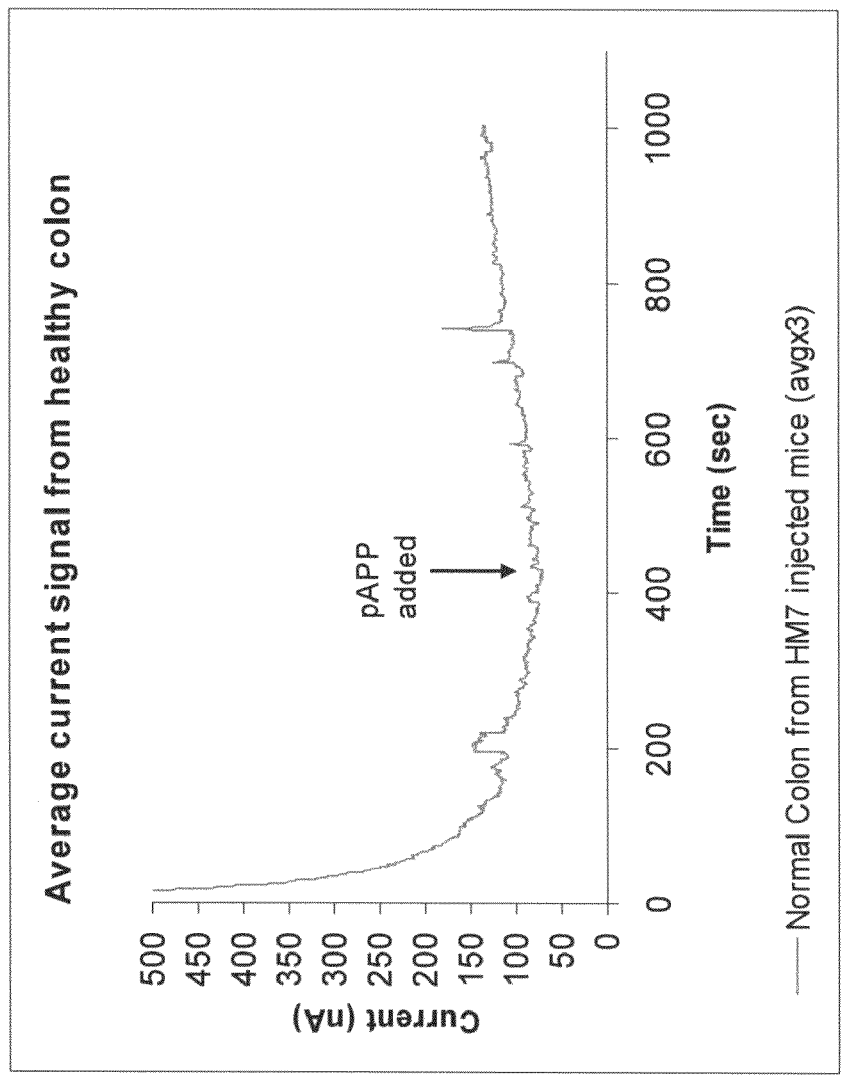

FIG. 11 is a graph illustrating the results of chronoamperometry analysis of healthy colon tissue (from HM7 injected mice). High background noise probably originates from contaminants present in colon contents. Current response upon pAPP addition is observed indicating the presence of alkaline phosphatase.

Figure 12:
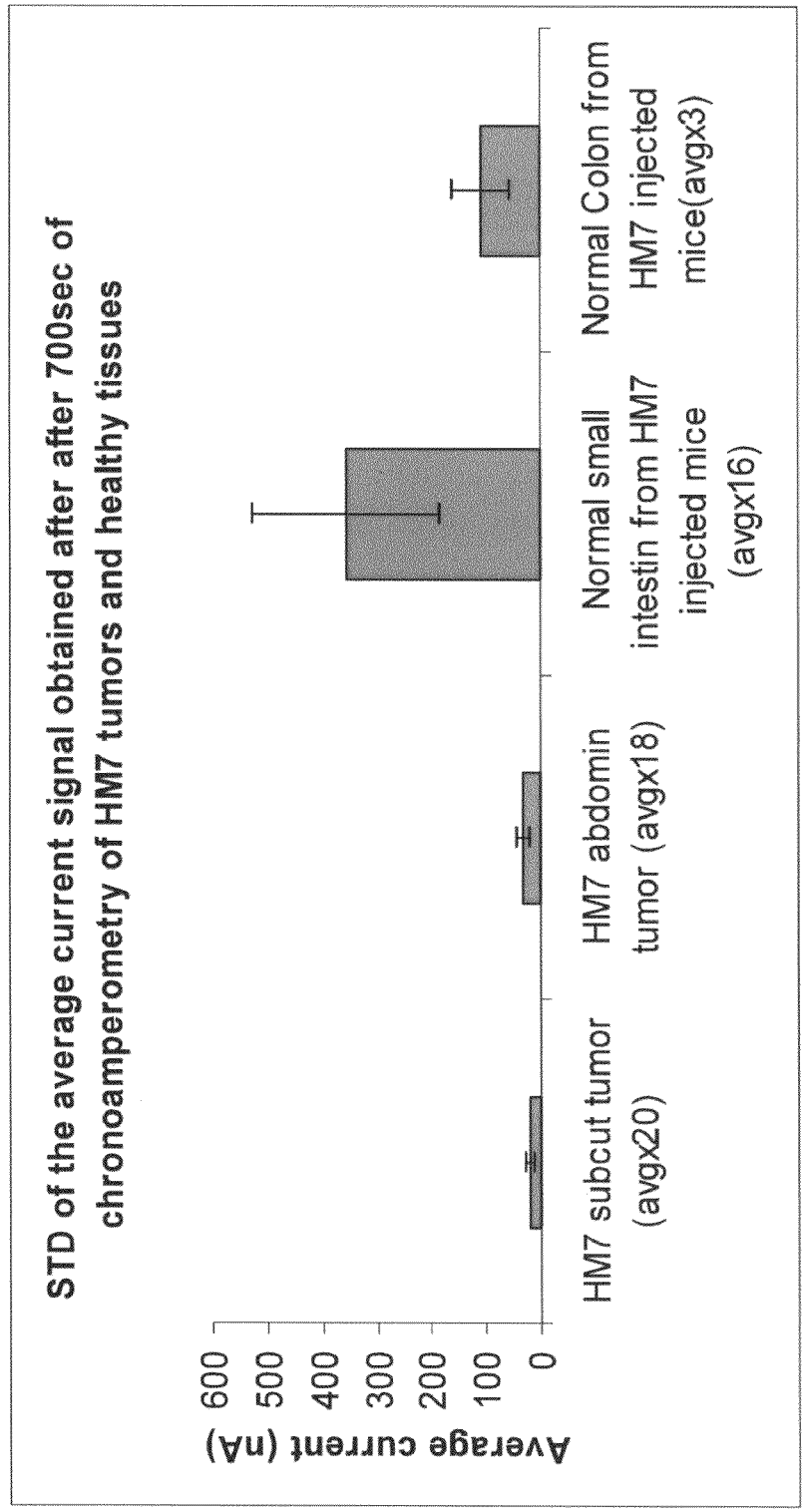

FIG. 12 is a graph illustrating the standard deviation from the average current signal obtained at 700 seconds (subcut=subcutaneous, abdomen=abdominal, avg=average) in HM7 and healthy tumor slices.

DESCRIPTION OF THE PREFERRED EMBODIMENTS

The present invention is of a method of detecting cancer cells. Specifically, the present invention can be used to diagnose cancer, monitor treatment, determine treatment regimens and develop novel treatment modalities for the disease.

The principles and operation of the method according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Differentiation therapy focuses on the induction of cancer cells to normal cells by forcing the cancer cells to resume a process of maturation. Numerous markers have been used as a means of monitoring patients undergoing differentiation therapy. One such marker is alkaline phosphatase, wherein expression of same was shown to correlate with the differentiation status of a cell. In general, normal enzymatic activity denotes that the cells differentiate properly as a consequence of the particular drug treatment, whilst lack of enzymatic activity denotes ineffectual drug treatment for the particular cancer and/or for the particular patient.

However, as yet there is no method for rapidly and easily detecting such markers with high sensitivity, selectivity and accuracy.

The present inventors have developed a novel electrochemical method for sensitive and high-throughput detection of a cancer cell's response to differentiation therapy.

Whilst reducing the present invention to practice, the present inventors have shown that amperometric enzyme measurements may be performed with electrochemical substrates such as p-APP in order to determine the effectiveness of a differentiation agent. As illustrated in FIG. 1, the effectiveness of three differentiation agents on human colon cancer cells was assessed using the method of the present invention. Using a chip that contained an array of miniaturized electrochemical cells, the present inventors were able to monitor the effectiveness of these differentiation therapy agents on a very small sample of cells (less than ~15 cells) in a highly sensitive, accurate and rapid fashion (FIGS. 2A-F and FIG. 3).

The drug effect could be measured with a resolution current response of ten nano Amperes within 5 minutes. Moreover, theses results demonstrate quantitative correlation between the induced current signals and the number of cancer cell counted inside the nano-volume chamber.

Utilizing nano-volume analytical device is of special interest in clinically relevant samples since it requires less tissue for diagnostics, and enables high-throughput analysis and comparison of the effect of various drugs on one tumor sample, while keeping uniform biological and environmental conditions. In addition, this new method can help tailor cancer drugs and treatments to individual patients towards 'personalized medicine'.

Thus, according to one aspect of the present invention, there is provided a method of detecting a cancer cell. The method comprises contacting the cell with a substrate for an enzyme, under conditions wherein the enzyme catalyzes a reaction of the cell with the substrate, so as to generate a product capable of producing an electrical signal and subsequently, measuring a level of the electrical signal, wherein a difference in a level of the electrical signal compared to a predetermined threshold is indicative of a cancer cell.

The term "detecting", as used herein, refers to the act of detecting, diagnosing, perceiving, uncovering, exposing, visualizing or identifying a cell.

As used herein, the term "cell" refers to a mammalian cell, preferably a human cell. Single cells may be used in accordance with the teachings of the present invention as well as plurality of cells. According to an exemplary embodiment, the plurality of cells comprises no less than 10 cells and no more than 500 cells. According to another exemplary embodiment the cells are in a single suspension such that the number of cells may be counted, although adherent cells and aggregates may still be detected. According to another exemplary embodiment tissue slices are analyzed.

The plurality of cells may be from any biological sample such as cell-lines, primary cultures and cellular samples, e.g. biopsies (surgical biopsies including incisional or excisional biopsy, fine needle aspirates and the like), complete resections or body fluids. Methods of biopsy retrieval are well known in the art.

According to one embodiment, following biopsy, a tumor sample is sliced. In order to calibrate the system, such that comparison between healthy and non-healthy slices is accurate, the tumor slices may be weighed.

The cells in the biological sample may be assayed for a functional enzyme without any pretreatment. Thus, the cells in the biological sample are preferably intact (i.e. whole), and preferably viable, although it will be appreciated that pretreatment of cells, such as generation of cell extracts or non-intact cells are also contemplated by the present invention.

A "cancer cell", also referred to herein as a "malignant cell", is a cell which has been released from normal cell division control, and is thus characterized by an abnormal growth and a tendency to proliferate in an uncontrolled way and, in some cases, to metastasize. Accordingly, the cancer cell may be a neoplastic cell, a pre-malignant cell, a metastatic cell, a tumor cell, an oncogenic cell, a cell with a cancer genotype, a cell of malignant phenotype, an oncogene transfected cell, a virus transformed cell, a cell which expresses an oncogene, a cell which expresses a marker for cancer, or a combination thereof.

Non-limiting examples of a cancer cell which may be detected by the method of the present invention is: an adenocarcinoma cell, an adrenal gland tumor cell, an ameloblastoma cell, an anaplastic cell, anaplastic carcinoma of the thyroid cell, an angiofibroma cell, an angioma cell, an angiosarcoma cell, an apudoma cell, an argentaffmoma cell, an arrhenoblastoma cell, an ascites tumor cell, an ascitic tumor cell, an astroblastoma cell, an astrocytoma cell, an ataxia-telangiectasia cell, an atrial myxoma cell, a basal cell carcinoma cell, a benign tumor cell, a bone cancer cell, a bone tumor cell, a brainstem glioma cell, a brain tumor cell, a breast cancer cell, a Burkitt's lymphoma cell, a cancerous cell, a carcinoid cell, a carcinoma cell, a cerebellar astrocytoma cell, a cervical cancer cell, a cherry angioma cell, a cholangiocarcinoma cell, a cholangioma cell, a chondroblastoma cell, a chondroma cell, a chondrosarcoma cell, a chorioblastoma cell, a choriocarcinoma cell, a colon cancer cell, a common acute lymphoblastic leukemia cell, a craniopharyngioma cell, a cystocarcinoma cell, a cystofbroma cell, a cystoma cell, a cytoma cell, a ductal carcinoma in situ cell, a ductal papilloma cell, a dysgerminoma cell, an encephaloma cell, an endometrial carcinoma cell, an endothelioma cell, an ependymoma cell, an epithelioma cell, an erythroleukemia cell, an Ewing's sarcoma cell, an extra nodal lymphoma cell, a feline sarcoma cell, a fibro adenoma cell, a fibro sarcoma cell, a follicular cancer of the thyroid cell, a ganglioglioma cell, a gastrinoma cell, aglioblastoma multiform cell, a glioma cell, a gonadoblastoma cell, an haemangioblastomacell, an haemangioendothelioblastoma cell, an haemangioendothelioma cell, an haemangiopericytoma cell, an haematolymphangioma cell, an haemocytoblastoma cell, an haemocytoma cell, a hairy cell leukemia cell, a hamartoma cell, an hepatocarcinoma cell, an hepatocellular carcinoma cell, an hepatoma cell, an histoma cell, a Hodgkin's disease cell, an hypemephroma cell, an infiltrating cancer cell, an infiltrating ductal cell carcinoma cell, an insulinoma cell, a juvenile angioforoma cell, a Kaposi sarcoma cell, a kidney tumor cell, a large cell lymphoma cell, a leukemia cell, a chronic leukemia cell, an acute leukemia cell, a lipoma cell, a liver cancer cell, a liver metastases cell, a Lucke carcinoma cell, a lymphadenoma cell, a lymphangioma cell, a lymphocytic leukemia cell, a lymphocytic lymphoma cell, a lymphoeytoma cell, a lymphoedema cell, a lymphoma cell, a lung cancer cell, a malignant mesothelioma cell, a malignant teratoma cell, a mastocytoma cell, a medulloblastome cell, a melanoma cell, a meningioma cell, a mesothelioma cell, a metastatic cell, a metastasis cell, a metastatic spread cell, a Morton's neuroma cell, a multiple myeloma cell, a myeloblastoma cell, a myeloid leukemia cell, a myelolipoma cell, a myeloma cell, a myoblastoma cell, a myxoma cell, a nasopharyngeal carcinoma cell, a neoplastic cell, a nephroblastoma cell, a neuroblastoma cell, a neurofibroma cell, a neurofibromatosis cell, a neuroglioma cell, a neuroma cell, a non-Hodgkin's lymphoma cell, an oligodendroglioma cell, an optic glioma cell, an osteochondroma cell, an osteogenic sarcoma cell, an osteosarcoma cell, an ovarian cancer cell, a Paget's disease of the nipple cell, a pancoast tumor cell, a pancreatic cancer cell, a phaeochromocytoma cell, a pheoehromocytoma cell, a plasmacytoma cell, a primary brain tumor cell, a progonoma cell, a prolactinoma cell, a renal cell carcinoma cell, a retinoblastoma cell, a rhabdomyosarcoma cell, a rhabdosarcoma cell, a solid tumor cell, sarcoma cell, a secondary tumor cell, a seminoma cell, a skin cancer cell, a small cell carcinoma cell, a squamous cell carcinoma cell, a strawberry haemangioma cell, a T-cell lymphoma cell, a teratoma cell, a testicular cancer cell, a thymoma cell, a trophoblastic tumor cell, a tumorigenic cell, a tumor initiation cell, a tumor progression cell, a vestibular schwannoma cell, a Wilm's tumor cell, or a combination thereof.

According to a preferred embodiment of this aspect of the present invention, the cancer cell is a colon cancer cell.

As mentioned hereinabove, the method of the present invention is effected by contacting an enzyme substrate with a cell, to bring about a reaction of the cell, wherein the product of the enzymatic reaction is capable of generating an electrical signal.

As used herein, the phrase "reaction of the cell" refers to a reaction that occurs between the substrate and an endogenous enzyme expressed by the cell, and not to a reaction that occurs with an exogenous enzyme.

The substrate is selected according to the enzyme, (also referred to herein as "marker enzyme") that is required to be detected. The enzyme may be situated inside the cell (i.e. intracellular) or on the cell membrane (i.e. membrane bound). According to another embodiment, the enzyme is a secreted enzyme. It will be appreciated that when the enzyme to be detected is intracellular, the substrate is preferably membrane permeable. Furthermore, the substrate is preferably selected such that following catalysis, the product formed is also membrane permeable such that it may diffuse away from the cell and on to the detector electrode According to one embodiment, the enzyme required to be detected is alkaline phosphatase (or enzyme secreted alkaline phosphatase, (SEAP)) and the substrate is 4-aminophenyl phosphate (p-APP). Alkaline phosphatase converts p-APP to the electrochemical product, p-aminophenol (PAP).

P-APP is widely commercially available from such Companies as Sigma-Aldrich (www.sigmaaldrich.com), Bioworld (www.Bio-world.com) and many others.

Alkaline phosphatase is present in normal cells, but is reduced (or even absent) in cancerous cells. Therefore, analysis of the alkaline phosphatase activity level of cells, may be used as a marker for evaluating the efficiency of a particular drug for treating cancer and even for diagnostic purposes.

As used herein, the term "contacting" refers to bringing the substrate into the vicinity of a cell under conditions such that the substrate may be catalyzed by the enzyme. Thus, for example, the contacting should by effected under buffer conditions, at a temperature and time sufficient to allow catalysis of the substrate and generation of sufficient product that it may be detected by an electrochemical cell. For example, when p-APP is used as a substrate, preferably the contacting is effected for at least 5 minutes, at room temperature—see Examples 2 and 3 herein below.

The contacting may be effected in vitro, ex vivo or in vivo. The contacting may be effected in a vessel which is also capable of detecting the product of the enzymatic reaction (i.e., in the electrochemical cell), such that the electrical signal is detected on-line. Such vessels are further described herein below. Alternatively, the contacting may be effected in a separate vessel from where the detection takes place such that it is possible to continuously withdraw samples at particular time points and place such samples within the electrochemical cells. Thus, the contacting may be effected in a test tube, flask, tissue culture, chip, array, plate, microplate, capillary, or the like. The cells may be placed on a vibrating plate following the addition of the substrate for continuous thorough mixing of the contents of the cells.

As mentioned hereinabove, electrochemical measurement of products capable of undergoing a redox reaction (i.e. capable of electron transfer) at an electrode of a chemical cell to yield an electrical signal (i.e. electrochemical products) is typically effected in electrochemical cells.

As used herein, the phrase "electrical signal" refers to electrons or electrochemically active species.

The phrase "electrochemical measurement" as used herein, refers to a measurement performed by the use of electrodes in a solution, typically in an electrochemical cell. The measurement may be performed, for example, by chrono-amperometry, chrono-potentiometry, cyclic voltammetry, chrono-coulometry or square wave voltammetry. A signal detectable in such a measurement, is one that differs in such electrochemical measurement from the control.

For on-line measurement, the electrochemical cells of the present invention comprise a measurement electrode, a return electrode, a reference electrode and a chamber to hold the cells.

The working electrode may be of a variety of different kinds, for example, it may be made of carbon, including glassy carbon, activated carbon cloth electrode, carbon felt, platinized carbon cloth, plain carbon cloth), may be made of gold, platinum or silver. The counter electrode may also be made of the same material as the working electrode. The reference electrode may for example be saturated calomel electrode, may be an Ag/AgCl electrode. Furthermore, the electrodes may be of a screen printed electrode which can be inserted into the vessel comprising the cells without the need to withdraw a sample and transport it into a separate electrochemical cell.

The electrodes used to detect the product according to the method of the present invention may be reusable electrodes or disposable ones. Reusable electrodes may for example be electrodes made of glassy carbon in a disk or rod shape which are embedded in teflon. Disposable electrodes may for example be electrodes in the form of carbon paper, carbon cloth, carbon felts, or the screen printed electrode of the kind noted above.

According to one embodiment, the electrochemical cell is a three-electrode cell. According to another embodiment, the electrochemical cell is a two-electrode cell. According to a preferred embodiment the electrochemical cells are provided as an array (i.e. chip) comprising a plurality of such cells i.e. a multiwell array where each well is of a nano-volume size.

The system for measuring the electrical signal generated by the reaction product may further comprise a control module which may be a computer, a potentiostat and a multiplexer module which is needed in case of a typical embodiment for simultaneous measurement from a plurality of electrochemical cells.

The electrochemical measurement performed in the cell will now be described in reference to the chrono-amperometric mode. As will be appreciated, it applies, mutatis, mutandis also to the other electrochemical measurement modes mentioned above. Furthermore, the description will be made with reference to the use of a multi-electrode system (the system comprising an may of electrodes) and it is clear that it applies to a system comprising a single cell as well.

In the beginning of the electrochemical measurement all the electrodes are operated together, and the computer scans all the electrodes via the parallel port, and the background response to the potential application of each electrode is recorded by the computer. The entire electrochemical measurement sequence can be performed over a long period of time while measuring the currents resulting from the changes in the concentration of the products. In cases where the electrodes' surfaces are not identical due to natural variability, the system can be calibrated by measuring the oxidation or reduction of an electroactive species, typically the same species which is the product of the enzymatic reaction in the electrochemical cell and comparison of the results of all the electrodes.

In performing the assay, the electrodes may be connected to the potentiostat and at the same time also collected via the multiplexer to a parallel port of the microcomputer.

Each electrode is inserted in an electrochemical cell containing a reference electrode and a counter electrode which are also connected to the potentiostat. A specific potential is applied by the potentiostat on the electrodes (which can be the same for all the electrodes or can be a different potential to each electrode) and the current in each electrode is detected. The electrical signals are visualized in real-time on the computer screen.

Since the electrical signals generated by the electrochemical products of the enzymatic reactions reflect the level of enzyme in the cell, and the enzymes (presence, absence or level of same) are markers for cancer, the signals may be used to determine whether a cell is cancerous (i.e. malignant) or not. Specifically, if the level of the generated electrical signal is different to a predetermined threshold, this would indicate that the cell is cancerous. Typically, the predetermined threshold is determined by the electrical signal generated by a control cell.

The control cell can be a normally differentiated cell, non-cancerous cell, preferably of the same tissue and specimen as the tested cell suspicious of a cancerous or undifferentiated phenotype. Preferably, the difference is at least 10%, 20%, 30%, 40%, 50%, 80%, 100% (i.e., two-fold), 3 fold, 5 fold or 10 fold different as compared to a control cell.

According to one embodiment of the present invention, the amount of enzyme (and accordingly electrical signal) in a cancer cell is lower than the amount of enzyme (and accordingly electrical signal) in a non-cancer cell.

According to another embodiment of the present invention, the amount of enzyme (and accordingly electrical signal) in a cancer cell is higher than the amount of enzyme (and accordingly electrical signal) in a non-cancer cell.

It will be appreciated that the method of the present invention may be used for diagnosing a subject with cancer.

As used herein the term "diagnosing" refers to classifying a cancer, determining a severity of cancer (grade or stage), monitoring cancer progression, forecasting an outcome of the cancer and/or prospects of recovery.

The subject may be a healthy animal or human subject undergoing a routine well-being check up. Alternatively, the subject may be at risk of having cancer (e.g., a genetically predisposed subject, a subject with medical and/or family history of cancer, a subject who has been exposed to carcinogens, occupational hazard, environmental hazard] and/or a subject who exhibits suspicious clinical signs of cancer [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness).

It will be appreciated that the present has a variety of applications pertaining to individually optimizing a treatment for cancer, monitoring an-anti cancer treatment in a subject, determining an anti cancer treatment for a subject and identifying an agent capable of reversing a malignant phenotype of a cell.

Thus, according to another aspect of the present invention, there is provided a method of identifying an agent capable of reversing a malignant phenotype of a cell. The method comprises subjecting at least one cancer cell to an agent and determining the efficiency of the anti cancer agent by monitoring the activity or expression of the marker enzyme (e.g. alkaline phosphatase) according to the method of the present invention.

As used herein the phrase "reversing a malignant phenotype" refers to at least partially reversing the proliferative and/or invasive characteristics of the malignant cell.

As used herein, the term "agent" refers to a test composition comprising a biological agent or a chemical agent Examples of biological agents that may be tested as potential anti cancer agents according to the method of the present invention include, but are not limited to, nucleic acids, e.g., polynucleotides, ribozymes, siRNA and antisense molecules (including without limitation RNA, DNA, RNA/DNA hybrids, peptide nucleic acids, and polynucleotide analogs having altered backbone and/or bass structures or other chemical modifications); proteins, polypeptides (e.g. peptides), carbohydrates, lipids and "small molecule" drug candidates. "Small molecules" can be, for example, naturally occurring compounds (e.g., compounds derived from plant extracts, microbial broths, and the like) or synthetic organic or organometallic compounds having molecular weights of less than about 10,000 daltons, preferably less than about 5,000 daltons, and most preferably less than about 1,500 daltons.

According to a preferred embodiment of this aspect of the present invention the agents are differentiation agents including, but not limited to butyric acid and its derivatives.

Examples of conditions that may be tested as potential anti cancer agents according to the method of the present invention include, but are not limited to, radiation exposure (such as, gamma radiation, UV radiation, X-radiation).

According to an embodiment of this aspect of the present invention, the "marker enzyme" is also assayed prior to contact with the agent so that a comparison may be made prior to and following treatment.

According to another embodiment of this aspect of the present invention, the agent is subjected to the cancer cells for a period long enough to have an anti cancer effect. Thus, for example if butyric acid and/or its derivatives are being analyzed, preferably these agents are subjected to the cancer cells for at least 1 day and more preferably 3 days.

It will be appreciated that the agent may be contacted with cancer cells either in vitro, ex vivo or in vivo. If the contacting is effected in vivo, the cells are typically removed from the subject prior to contact with the substrate of the present invention.

Although the present invention can, in theory, be practiced with a single electrochemical cell, such a method is not efficient nor is it desirable. Preferably, the method of the present invention is used for high throughput screening of agents using a plurality of electrochemical cells to simultaneously screen a variety of agents. The cells may be part of a chip, for example a silicon chip as described in Example 1 herein below.

Thus, according to one embodiment, the method of the present invention is performed using means for high output. Accordingly, the method may be performed, for example, using an automated sampling device, a liquid handling equipment, a dispenser, an electrode array, a robot, or any combination thereof.

It is now known that tumor treatment response cannot be predicted only from its type and anatomical location. It will be appreciated that the method of identifying an agent capable of reversing a malignant phenotype of a cell may be modified such that particular patient's cells may be used in the assay system, thereby tailoring therapeutic agents to specific patients. Furthermore, it will be appreciated that not only may the specific agent be selected using the method of the present invention, but the optimal dose and optimal treatment regimen may also be identified according to the method of the present invention. In this way a therapeutically effective amount of an agent may be determined.

The patient may be treated according to the optimal treatment conditions selected with the aid of the method of the present invention and optionally retested after a suitable time period. In this way a patient's response may be continually monitored whilst undergoing therapy.

Conceivably the analyzing enzyme levels and administering steps may be repeated a number of times during the course of a treatment. For instance the alkaline phosphatase levels may be analyzed one week following administration of the agent. If the alkaline phosphatase levels are higher than those compared with a control, the dose of the agent may be decreased. If the alkaline phosphatase levels remain lower than those compared with a control, the dose of the agent may be increased.

It will be appreciated that the electrochemical cell of the present invention may be provided in a kit together with at least one anti-cancer agent (e.g. a differentiation agent such as butyric acid) for determining an effect thereof on a cancer cell. The kit of the present invention may, if desired, be presented in a pack which may contain one or more units of the kit of the present invention. The pack may be accompanied by instructions for using the kit and the estimated dose of the anti-cancer agent for a particular number of cells. The pack may also be accommodated by a notice associated with the container in a form prescribed by a governmental agency regulating the manufacture, use or sale of laboratory supplements, which notice is reflective of approval by the agency of the form of the compositions.

According to one embodiment, the kit may also comprise a substrate which is enzymatically reacted on by the marker enzyme of the biological cell (i.e. cancer cell) to yield a reaction product giving rise to a redox reaction at an electrode of the electrochemical cell. Such substrates have been described herein above.

It is expected that during the life of this patent many relevant substrates will be developed and the scope of the term substrate is intended to include all such new technologies a priori.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Manufacture of the Nano-Bio-Chip

A nano-bio-chip was designed and fabricated using standard micro-system-technology (MST) methods. Its architecture included an array of miniaturized electrochemical cells. The cells were placed in the nano-volume chambers (i.e. the electrochemical-cells). The cylindrical chambers held 100 nL volume each. All arrays included positive and negative controls chambers.

The device was manufactured in two parts: a) a disposable chip—with the nano-chambers where the cells were placed, and b) a reusable chip, with an interface to electronic circuitry which included a multiplexer, potentiostat, temperature control and a pocket PC for sensing and data analysis. This setting allowed continuous reusing for multiple measurements.

The chip was produced from silicon, and contained an array of eight miniaturized electrochemical cells. Each electrochemical-cell consisted of three circular-shaped electrodes, surrounded by an insulating silicon nitride layer: 1) Gold working electrode, 2) Gold counter electrode and 3) Ag/AgCl reference electrode. The electrodes were made by gold sputtering, microlithography and by selectively depositing Ag and anodizing it in a chloride containing solution for the reference electrode. The chambers walls were constructed from photopolymerized polyimide (SU-8) (FIGS. 1A-B). The silicon chip was wire bonded to a plastic chip, which was interfacing the electronic circuit.

The signal sensing was performed by the handheld palm-potentiostat with an interface to electronic circuitry for electrode signal regulation and detection (Palm Instruments BV-2004). The electronics consisted of eight independent duplicate circuits of electrochemical cells, which are temperature-controlled. A potential was applied between a working and a reference electrode in each electrochemical cell, and the output current was measured.

General Materials and Methods for Examples 2 and 3 Below

Cell lines and cultures: HT-29 human colon cancer cells were grown in DMEM medium in the presence of fetal bovine serum at 37° C. in 95% air, 5% $CO_2$ for 3 days prior to butyrate treatment. Butyrate at different concentrations was added to the HT-29 cell cultures. Concentrations applied were: 0, 0.078, 0.156, 0.3125, 0.625, 1.25, 2.5, 5 and 10 mM. Optimal butyrate concentration, LC50 and viability were calculated accordingly. The measurements were performed in PBS with the intact cells and without additional treatment of the cancer cells such as lysis.

Butyric acid (BA) and its derivatives: BA (Sigma, Israel) ranging between 0.08-10 mM were introduced to HT-29 colon cancer cells and incubated for 72 h for optimization. BA at a constant concentration of 2.5 mM was applied in all electrochemical experiments. BA derivatives, butyroylmethyl-diethyl phosphate, and pivaloyloxymethyl butyrate, were synthesized as described [Rephaeli A, Zhuk R, Nudelman A, 2000, Drug Develop. Res. Vol 50:379-391]. Butyroylmethyl-diethyl phosphate was solubilized in PBS and pivaloyloxymethyl butyrate in DMSO followed by dilution with medium to a final DMSO concentration of ≦0.1%. The prodrugs were then introduced to the cells at a constant concentration of 50 μM and incubated for 96 h at 37° C. in 95% air, 5% $CO_2$ conditions. Following incubation with the differentiation agents, viable cells were counted by tripa blue exclusion and tested for viability and $LC_{50}$ calculations. Prior to all electrochemical measurement, cells were centrifuged and diluted in PBS. All measurements were performed in PBS. The influence of BA, pivaloyloxymethyl butyrate and butyroylmethyl-diethyl phosphate were examined by measuring the enzymatic activity of alkaline phosphatase.

Alkaline Phosphatase Activity Measurements:

Optical measurements: Alkaline phosphatase activity was detected with the optical substrate para-Nitrophenyl Phosphate (PNPP kit ready to use, Sigma). The resultant enzymatic product was measured at wavelength of 420 nm.

Electrochemical measurements: Amperometric enzyme measurements were performed with the electrochemical substrate, p-APP. The enzymatic reaction product, aminophenol (p-AP), is oxidized at the gold working electrode at 220 mV and the generated current was measured. Eight-channeled 100 nL volume electrochemical chambers were loaded with HT-29 cancer cells, that were treated with BA or its derivatives. Cells were placed into the electrochemical chambers and the substrate was added to 1 mg/ml final concentration at a total volume of 100 mL. The generated current was measured and the number of cells was counted under the microscope. The correlation between cell number and current density was analyzed.

Example 2

Effect of Drugs on Colon Cancer Cells as Assayed by the Biochip of the Present Invention In order to individualize cancer therapy, the influence of various single-source drugs on human colon cancer cells (HT-29), was examined.

Results

HT-29 colon cancer cells were exposed for 96 hours to various differentiation therapy agents and the induced alkaline phosphatase activity was measured. Each electrochemical chamber on the array was loaded with cells exposed to a different agent—namely Butyric acid, butyroylmethyl-diethyl phosphate and pivaloyloxymethyl butyrate. The results are shown in FIG. 1A-C. Normal enzymatic activity denotes that the cells differentiate properly as a consequence of the particular drug treatment. As shown in FIGS. 1A-C, BA and butyroylmethyl-diethyl phosphate induced enzymatic activity of alkaline phosphatase, whilst pivaloyloxymethyl butyrate did not induce any enzyme activity at 50 μM concentration exposure, which may be related to its reduced potency regarding HT-29 cancer cells [M. Entin-Meer, et al., Molecular Cancer Therapeutics, vol. 4, pp. 1952-1961, 2005; D. Engel, et al., Clinical Cancer Research, vol. 11, pp. 9052S-9052S, 2005]. In addition, positive and negative controls were performed: Chambers were loaded with drug-treated cells, untreated cells as negative control and purified alkaline phosphatase as positive control. It is important to note that butyroylmethyl-diethyl phosphate exerted similar differentiation effect to the BA although its concentration was lower by 1.5 orders of magnitude, 50 μM Vs. 2.5 mM for butyroylmethyl-diethyl phosphate and BA, respectively.

Example 3

Quantification of Cancer Cells by the Biochip

Results

A remarkable quantitative correlation between the induced current signals and the number of cancer cells counted inside the nano-volume chamber was detected. Numeration of the cancer cells and the relative enzymatic activity are shown in FIGS. 2A-F. Amperometric response curves for monitoring of alkaline phosphatase activity were generated using the electrochemical array chip. The HT-29 colon cancer cells were exposed to Butyric acid (2.5 mM). The HT-29 cells with the substrate PAPP were placed into the 100 mL volume electrochemical chambers on the chip. Current was measured using the amperometric technique at 220 mV. Upper middle and lower curves represent the current response of about 100 cells, 15 and 0 cells counted inside the chamber, respectively. Multiple measurements demonstrated high correlation between cell number counted inside the chamber and alkaline phosphatase activity. The results are shown in FIG. 3. The ability to quantitate the enzymatic reaction is due to the miniaturized design of the chip, combined with the advantages of the electrochemical detection method.

Example 4

Effect of Butyroylmethyl-Diethylphosphate on Colon Cancer Cells as Assayed by the Biochip of the Present Invention In order to further examine the sensitivity of the biochip, increasing numbers of HT-29 colon cancer cells were incubated with butyroylmethyl-diethyl phosphate for different lengths of time. The amount of endogenous alkaline phosphatase was measured using the biochip of the present invention.

Results

The results are shown in FIGS. 4A-C, 5A-C and 6A-C. The effect of butyroylmethyl-diethyl phosphate on the cancer cells increased as incubation time increased. In addition, it can be seen that the magnitude of the effect correlated with the number of cells examined.

Conclusions

A new method for sensitive and high-throughput detection of cancer cells in response to differentiation therapy has been demonstrated. In the case of human colon cancer cells, these cells were treated with different differentiation therapy drug agents, and cell response to different drugs was simultaneously and on line measured. This microarray technology provides the ability to test on line multi-drug agents, and to tailor effective therapy to the individual.

This 'Lab-on-a-chip' system provides the ability of sensitive measurements on extremely small samples (less than ~15 cells) and does not require special cell treatment prior to the insertion into the chip.

Example 5

Analysis of Tumor Slices Using the Biochip of the Present Invention

Materials and Methods

For demonstration of feasibility of analyzing tumor slices, two cancer cell lines were injected to nude mice, representing two different subtypes of colon cancer.

Cancer cell lines and mice: HCT116 and HM7 cell lines were injected, separately, to athymic nude mice at different locations: subcutaneous and abdominal. For feasibility demonstration two different colorectal cell lines were used, representing two subtypes. HCT116, the epithelial human colon carcinoma cell line, tumorigenic in athymic nude mice, and the metastatic HM7, a human colon cancer cell line which is a clone selected from LS174T cells and is characterized by high mucin production. This variant is highly metastatic and correlates with poor prognosis.

Tumors were allowed to develop and mice were sacrificed within 6 weeks. Subcutaneous HCT116 tumors were collected from 6 mice, and abdominal tumors from 3 mice. Subcutaneous HM7 tumors were collected from 3 mice, and abdominal tumors from 3 mice. For control, slices from healthy small intestine were taken from 4 HCT116-injected mice and from 3 HM7-injected mice. Also, slices from healthy colon tissue were removed from 2 HCT116-injected mice and from 1 HM7-injected mouse.

Altogether, as many as 19 samples of subcutaneous tumors were tested HCT116 tumor-bearing mice and 16 abdominal tumor samples were tested from HCT116 tumor-bearing mice, From HM7 tumor-bearing mice, 20 samples of subcutaneous tumors were tested and 20 abdominal tumor samples. 32 samples of healthy small intestine tissue and 16 from colon were tested.

Tumor treatment prior to measurement: Following removal, tumors were incubated in cell medium (DMEM 88%, fetal calf serum 10%, glutamine 1% and antibiotics 1% all purchased from "Beit Haemek biological industries Israel") at room temperature, in sealed 50 ml tubes. Tumors were allowed to incubate for no more than 6 hours. Before measurements, tumors were washed 3 times in PBS and than dissected to slices of ~1-2 mm. tumor slices were weighed and placed in warm (37° C.) PBS until measured (not more than 1 hour).

Bioelectrochemical measurement: Chronoamperometry was performed in a conventional potentiostat equipped with an eight channel multiplexer at its input. The electrochemical chamber was constructed as a 300 μl chamber on screen printed electrodes (SPE) (custom made by Gwent, UK; Figure. Electrode configuration comprised a gold working electrode, a carbon auxiliary and Ag/AgCl reference electrodes. During measurements continuous mixing was applied.

Each tumor slice was placed in an electrochemical chamber, inside 220 μl PBS. All the electrodes were connected via the eight-channel multiplexer under mixing. A potential of 220 mV Vs. Ag/AgCl reference electrode was applied immediately prior to measurement. Following a short equilibration time (350 seconds), so as to allow the stabilization of the system and definition of the background signal (dominated by electrical and biochemical noise), the substrate pAPP (p-amino phenyl phosphate) was added (25 μl at a final concentration of ~0.1 mg/ml). The use of a multiplexer enabled the high capacity detection scheme resulting in multi sampling.

Results

Chronoamperometrical measurements of HCT116 tumors and healthy tissues was performed as described. Results demonstrated significant differences in current signal between the cancerous and healthy tissues, as seen in FIG. 8.

As shown, an electrochemical response was clearly visible after a few seconds. While tissues from healthy small intestine secrete the highest concentrations of alkaline phosphatase, tissues from healthy colon show a lower level of enzyme expression. However, current signal from tumor tissues are significantly lower and indicate the possible down regulation of alkaline phosphatase enzyme expression in cancer tissues. The steady increase in current, as seen in both healthy tissues, may suggest an active increase in enzyme expression which in turn implies that the tissues remain vital during measurement.

In light of the number of measurements, the standard deviation was calculated from the average current signal obtained after 800 seconds chronoamperometry. As illustrated in FIG. 9, although comprising various cell types, the method of the present invention demonstrates good reproducibility. Within 450 seconds following the addition of a substrate, it was possible to distinguish HCT116 tumors from healthy tissues.

Measurements of HM7 tissues was performed in the same manner and yielded results as illustrated in FIG. 10.

Similar to the case of HCT116, measurements of HM7 tumors indicated a very low level of alkaline phosphatase expression, while healthy small intestinal tissue exhibited current signal corresponding to high levels of the enzyme. Measurements of healthy colon tissue were characterized by a relatively high background noise, as illustrated in FIG. 11.

The high background noise observed in these colon measurements were probably due to contaminants in the colon present in the electrochemical chamber. It appears that when colon contents are present, some undesired electroactive species contribute to an electrochemical reaction at 0.22V. However, upon the addition of the substrate pAPP a clear current response was visible, responsible for an increase of up to double the noise signal.

The standard deviation from the average current signal was calculated in the measurements of these tumors as well, at a time point of 700 seconds from beginning of chronoamperometry as illustrated in FIG. 12.

Similar to HCT116 tumors, the expression level of alkaline phosphatase from HM7 tumors was very low relative to healthy small intestine. A recognizable current signal in healthy colon could be distinguished from the signal obtained from tumor tissue.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of detecting a colon cancer cell comprising:
   (a) contacting a cell from the colon which is suspicious of a cancerous or undifferentiated phenotype with 4-aminophenyl phosphate (p-APP) under conditions wherein alkaline phosphatase of the cell catalyzes a reaction with said p-APP, so as to generate a product which produces an electrical signal; and
   (b) measuring a level of said electrical signal, wherein a decrease in a level of said electrical signal compared to a predetermined threshold in a control cell is indicative of a colon cancer cell, thereby detecting the colon cancer cell.

2. A method of monitoring an anti cancer treatment in a subject, the method comprising:
   (a) administering at least one anti cancer agent to the subject; and
   (b) detecting a presence or level of cancer cells in a sample of the subject according to the method of claim 1, wherein said presence or level is indicative of a state of the cancer, thereby monitoring an anti-cancer treatment in a subject.

3. The method of claim 2, wherein said sample comprises a tissue.

4. The method of claim 2, wherein said cancer cells are intact.

5. The method of claim 2, wherein said cancer cells are mammalian cells.

6. The method of claim 1, wherein said measuring is performed using means for high throughput.

7. The method of claim 6, wherein said means is selected from the group consisting of an automated sampling device, a liquid handling equipment, a dispenser, an electrode array, a robot, or any combination thereof.

8. The method of claim 1, wherein said contacting is effected in vitro.

9. The method of claim 1, wherein said contacting is effected ex vivo.

10. The method of claim 1, wherein said measuring is effected using an electrochemical cell.

11. The method of claim 10, wherein said measuring is effected in a multiwell array.

12. The method of claim 11, wherein each well of said multiwell array comprises an electrochemical cell.

13. The method of claim 11, wherein each well of said multiwell array is a nano-volume well.

14. The method of claim 1, wherein said cell is intact.

15. The method of claim 1, wherein said cell is a mammalian cell.

16. A method of detecting a cancerous colon tissue comprising:
   (a) contacting a colon tissue which is suspicious of a cancerous or undifferentiated phenotype with p-APP under conditions wherein alkaline phosphatase of a cell of the tissue catalyzes a reaction of a cell with said p-APP, so as to generate a product which produces an electrical signal; and
   (b) measuring a level of said electrical signal, wherein a decrease in a level of said electrical signal compared to a predetermined threshold in a control tissue is indicative of the cancerous tissue, thereby detecting the cancerous colon tissue.

17. A method of diagnosing a subject with colon cancer comprising:
   (a) contacting at least one cell which is suspicious of a cancerous or undifferentiated phenotype in a colon sample of a subject with p-APP under conditions wherein alkaline phosphatase of said at least one cell catalyzes a reaction with said p-APP, so as to generate a product which produces an electrical signal; and
   (b) measuring a level of said electrical signal, wherein a decrease in a level of said electrical signal compared to a predetermined threshold in a control cell is indicative of colon cancer, thereby diagnosing the subject with colon cancer.

18. The method of claim 17, wherein said sample comprises a tissue.

19. The method of claim 1, wherein said at least one cell comprises a plurality of cells.

20. The method of claim 17, wherein said sample comprises no more than 500 cells.

21. The method of claim 17, wherein said sample comprises no less than 10 cells.

22. A method of individually optimizing a treatment for colon cancer, the method comprising:
   (a) contacting at least one cancer cell in a colon sample of a subject with at least one anti cancer agent;
   (b) contacting said at least one cancer cell with p-APP, under conditions wherein alkaline phosphatase of said at least one cell catalyzes a with said p-APP, so as to generate a product which produces an electrical signal; and
   (c) measuring a level of said electrical signal produced by the cell, wherein an increase in said level is indicative of an efficienct anti cancer agent for the treatment of the colon cancer of said subject, thereby individually optimizing a treatment for cancer.

23. The method of claim 22, wherein said sample comprises a tissue.

24. The method of claim 22, wherein said agent comprises a test composition.

25. The method of claim 24, wherein said test composition is selected from the group consisting of a polynucleotide a polypeptide, a small molecule chemical, a carbohydrate and a lipid.

26. The method of claim 22, wherein said agent comprises a test condition.

27. The method of claim 26, wherein said test condition is a radiation condition.

* * * * *